US008016783B2

United States Patent
Pastore et al.

(10) Patent No.: US 8,016,783 B2
(45) Date of Patent: Sep. 13, 2011

(54) METHOD AND APPARATUS FOR MODULATING CELLULAR METABOLISM DURING POST-ISCHEMIA OR HEART FAILURE

(75) Inventors: Joseph M. Pastore, Minneapolis, MN (US); Julio C. Spinelli, Shoreview, MN (US); Helen L. Reeve, St. Paul, MN (US); Jeffrey Ross, Roseville, MN (US); Rodney W. Salo, Fridley, MN (US); Allan Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 530 days.

(21) Appl. No.: 11/998,969

(22) Filed: Dec. 3, 2007

(65) Prior Publication Data

US 2008/0091138 A1    Apr. 17, 2008

Related U.S. Application Data

(62) Division of application No. 10/645,823, filed on Aug. 21, 2003, now Pat. No. 7,320,675.

(51) Int. Cl.
*A61M 31/00* (2006.01)
(52) U.S. Cl. ........................................................ 604/67
(58) Field of Classification Search .................. 604/67
See application file for complete search history.

(56) References Cited

U.S. PATENT DOCUMENTS 3,692,027 A    9/1972    Ellinwood, Jr.
(Continued)

FOREIGN PATENT DOCUMENTS

EP    0054138 A1    6/1982
(Continued)

OTHER PUBLICATIONS

"U.S. Appl. No. 10/742,574, filed Apr. 15, 2010 to Final Office Action dated Jan. 15, 2010", 12 pgs.

(Continued)

*Primary Examiner* — Nicholas D Lucchesi
*Assistant Examiner* — Jason Flick
(74) *Attorney, Agent, or Firm* — Schwegman, Lundberg & Woessner, P.A.

(57) ABSTRACT

A drug delivery system detects a cardiac condition indicative of a need for increasing a cardiac metabolic level and, in response, releases a drug into tissue or blood to shift a source of metabolically synthesized energy fueling cardiac contraction from fatty acid to glucose. One example of such a system includes an implantable device detecting an ischemia and a transdermal drug delivery device delivering a drug when an ischemic condition is detected. Another example of such a system includes one or more implantable devices detecting a predefined change in cardiac metabolic level and delivering a drug when the change is detected. Such systems are applied to treat, for example, patients suffering ischemia and/or heart failure and patients having suffered myocardial infarction.

20 Claims, 8 Drawing Sheets

U.S. PATENT DOCUMENTS

| | | | |
|---|---|---|---|
| 4,003,379 A | 1/1977 | Ellinwood, Jr. | |
| 4,137,908 A | 2/1979 | Degonde et al. | |
| 4,146,029 A | 3/1979 | Ellinwood, Jr. | |
| 4,281,664 A | 8/1981 | Duggan | |
| 4,299,220 A | 11/1981 | Dorman | |
| 4,470,987 A | 9/1984 | Wurtman et al. | |
| 4,544,371 A | 10/1985 | Dormandy, Jr. et al. | |
| 4,556,063 A | 12/1985 | Thompson et al. | |
| 4,559,946 A | 12/1985 | Mower | |
| 4,561,443 A | 12/1985 | Hogrefe et al. | |
| 4,674,518 A | 6/1987 | Salo | |
| 4,686,987 A | 8/1987 | Salo et al. | |
| 4,693,253 A | 9/1987 | Adams | |
| 4,871,351 A | 10/1989 | Feingold | |
| 4,880,005 A | 11/1989 | Pless et al. | |
| 4,897,987 A | 2/1990 | Spalla | |
| 4,901,731 A | 2/1990 | Millar | |
| 4,904,472 A | 2/1990 | Belardinelli et al. | |
| 4,924,875 A | 5/1990 | Chamoun | |
| 4,930,075 A | 5/1990 | Kortas | |
| 4,944,299 A | 7/1990 | Silvian | |
| 4,980,379 A | 12/1990 | Belardinelli et al. | |
| 4,983,166 A | 1/1991 | Yamawaki | |
| 4,987,897 A | 1/1991 | Funke | |
| 5,002,052 A | 3/1991 | Haluska | |
| 5,014,698 A | 5/1991 | Cohen | |
| 5,040,533 A | 8/1991 | Fearnot | |
| 5,041,107 A | 8/1991 | Heil, Jr. | |
| 5,042,497 A | 8/1991 | Shapland | |
| 5,058,581 A | 10/1991 | Silvian | |
| 5,087,243 A | 2/1992 | Avitall | |
| 5,113,869 A | 5/1992 | Nappholz et al. | |
| 5,127,404 A | 7/1992 | Wyborny et al. | |
| 5,135,004 A | 8/1992 | Adams et al. | |
| 5,137,019 A | 8/1992 | Pederson et al. | |
| 5,184,614 A | 2/1993 | Collins et al. | |
| 5,190,035 A | 3/1993 | Salo et al. | |
| 5,199,428 A | 4/1993 | Obel et al. | |
| 5,215,083 A | 6/1993 | Drane et al. | |
| 5,220,917 A | 6/1993 | Cammilli et al. | |
| 5,269,301 A | 12/1993 | Cohen | |
| 5,282,836 A | 2/1994 | Kreyenhagen et al. | |
| 5,284,136 A | 2/1994 | Hauck et al. | |
| 5,305,745 A | 4/1994 | Zacouto | |
| 5,334,222 A | 8/1994 | Salo et al. | |
| 5,342,408 A | 8/1994 | deCoriolis et al. | |
| 5,347,241 A | 9/1994 | Panaretos et al. | |
| 5,353,800 A | 10/1994 | Pohndorf et al. | |
| 5,354,264 A | 10/1994 | Bae et al. | |
| 5,354,317 A | 10/1994 | Alt | |
| 5,366,485 A | 11/1994 | Kroll et al. | |
| 5,368,028 A | 11/1994 | Palti | |
| 5,391,190 A | 2/1995 | Pederson et al. | |
| 5,404,877 A | 4/1995 | Nolan et al. | |
| 5,405,362 A | 4/1995 | Kramer et al. | |
| 5,416,695 A | 5/1995 | Stutman et al. | |
| 5,417,717 A | 5/1995 | Salo et al. | |
| 5,431,682 A | 7/1995 | Hedberg | |
| 5,456,692 A | 10/1995 | Smith, Jr. et al. | |
| 5,460,605 A | 10/1995 | Tuttle et al. | |
| 5,487,752 A | 1/1996 | Salo et al. | |
| 5,496,360 A | 3/1996 | Hoffmann et al. | |
| 5,499,971 A | 3/1996 | Shapland et al. | |
| 5,531,768 A | 7/1996 | Alferness | |
| 5,540,728 A | 7/1996 | Shelton et al. | |
| 5,545,186 A | 8/1996 | Olson et al. | |
| 5,551,953 A | 9/1996 | Lattin et al. | |
| 5,556,421 A | 9/1996 | Prutchi et al. | |
| 5,558,632 A | 9/1996 | Lloyd et al. | |
| 5,562,711 A | 10/1996 | Yerich et al. | |
| 5,562,713 A | 10/1996 | Silvian | |
| 5,579,876 A | 12/1996 | Adrian et al. | |
| 5,584,868 A | 12/1996 | Salo et al. | |
| 5,586,556 A | 12/1996 | Spivey et al. | |
| 5,591,215 A | 1/1997 | Greenhut et al. | |
| 5,603,331 A | 2/1997 | Heemels et al. | |
| 5,607,418 A | 3/1997 | Arzbaecher | |
| 5,607,463 A | 3/1997 | Schwartz et al. | |
| 5,609,613 A | 3/1997 | Woodson et al. | |
| 5,632,766 A | 5/1997 | Hsu | |
| 5,634,899 A | 6/1997 | Shapland et al. | |
| 5,662,689 A | 9/1997 | Elsberry et al. | |
| 5,676,686 A | 10/1997 | Jensen et al. | |
| 5,683,424 A | 11/1997 | Brown et al. | |
| 5,690,682 A | 11/1997 | Buscemi et al. | |
| 5,693,075 A | 12/1997 | Plicchi et al. | |
| 5,703,125 A | 12/1997 | Bovy et al. | |
| 5,713,934 A | 2/1998 | Leckrone | |
| 5,720,770 A | 2/1998 | Nappholz et al. | |
| 5,730,125 A | 3/1998 | Prutchi et al. | |
| 5,733,313 A * | 3/1998 | Barreras et al. | 607/33 |
| 5,741,214 A | 4/1998 | Ouchi et al. | |
| 5,759,199 A | 6/1998 | Snell et al. | |
| 5,782,879 A | 7/1998 | Rosborough et al. | |
| 5,792,204 A | 8/1998 | Snell | |
| 5,800,498 A | 9/1998 | Obino et al. | |
| 5,807,306 A | 9/1998 | Shapland et al. | |
| 5,814,089 A | 9/1998 | Stokes et al. | |
| 5,817,131 A | 10/1998 | Elsberry et al. | |
| 5,833,603 A | 11/1998 | Kovacs et al. | |
| 5,836,935 A | 11/1998 | Ashton et al. | |
| 5,893,881 A | 4/1999 | Elsberry et al. | |
| 5,899,928 A | 5/1999 | Sholder et al. | |
| 5,906,633 A | 5/1999 | Mouchawar et al. | |
| 5,919,210 A * | 7/1999 | Lurie et al. | 607/3 |
| 5,925,066 A | 7/1999 | Kroll et al. | |
| 5,949,659 A | 9/1999 | Lesche | |
| 5,957,957 A | 9/1999 | Sheldon | |
| 5,967,986 A | 10/1999 | Cimochowski et al. | |
| 5,978,705 A | 11/1999 | KenKnight et al. | |
| 5,991,668 A | 11/1999 | Leinders et al. | |
| 6,016,443 A | 1/2000 | Ekwall et al. | |
| 6,016,447 A | 1/2000 | Juran et al. | |
| 6,016,448 A | 1/2000 | Busacker et al. | |
| 6,021,350 A | 2/2000 | Mathson | |
| 6,022,322 A | 2/2000 | Prutchi | |
| 6,052,614 A | 4/2000 | Morris, Sr. et al. | |
| 6,066,094 A | 5/2000 | Ben-Haim | |
| 6,076,015 A | 6/2000 | Hartley et al. | |
| 6,104,949 A * | 8/2000 | Pitts Crick et al. | 600/547 |
| 6,112,116 A | 8/2000 | Fischell et al. | |
| 6,112,117 A | 8/2000 | KenKnight et al. | |
| 6,115,636 A | 9/2000 | Ryan | |
| 6,117,296 A | 9/2000 | Thomson | |
| 6,128,526 A | 10/2000 | Stadler et al. | |
| 6,140,740 A | 10/2000 | Porat et al. | |
| 6,141,588 A | 10/2000 | Cox et al. | |
| 6,154,672 A | 11/2000 | Pendekanti et al. | |
| 6,154,675 A | 11/2000 | Juran et al. | |
| 6,155,267 A | 12/2000 | Nelson | |
| 6,161,042 A | 12/2000 | Hartley et al. | |
| 6,168,801 B1 | 1/2001 | Heil, Jr. et al. | |
| 6,184,030 B1 | 2/2001 | Katoot et al. | |
| 6,198,394 B1 | 3/2001 | Jacobsen et al. | |
| 6,200,265 B1 | 3/2001 | Walsh et al. | |
| 6,203,495 B1 | 3/2001 | Bardy | |
| 6,206,914 B1 | 3/2001 | Soykan et al. | |
| 6,212,434 B1 | 4/2001 | Scheiner et al. | |
| 6,213,942 B1 | 4/2001 | Flach et al. | |
| 6,221,011 B1 | 4/2001 | Bardy | |
| 6,231,516 B1 | 5/2001 | Keilman et al. | |
| 6,237,398 B1 | 5/2001 | Porat et al. | |
| 6,238,367 B1 | 5/2001 | Christiansen et al. | |
| 6,251,125 B1 | 6/2001 | KenKnight et al. | |
| 6,253,108 B1 | 6/2001 | Rosborough et al. | |
| 6,254,573 B1 | 7/2001 | Haim et al. | |
| 6,256,233 B1 | 7/2001 | Glass | |
| 6,256,541 B1 | 7/2001 | Heil et al. | |
| 6,259,949 B1 | 7/2001 | Rosborough | |
| 6,261,230 B1 | 7/2001 | Bardy | |
| 6,263,241 B1 | 7/2001 | Rosborough et al. | |
| 6,264,606 B1 | 7/2001 | Ekwall et al. | |
| 6,266,554 B1 | 7/2001 | Hsu et al. | |
| 6,270,457 B1 | 8/2001 | Bardy | |
| 6,272,377 B1 | 8/2001 | Sweeney et al. | |
| 6,277,072 B1 | 8/2001 | Bardy | |
| 6,277,078 B1 | 8/2001 | Porat et al. | |

| | | | |
|---|---|---|---|
| 6,278,894 B1 | 8/2001 | Salo et al. | |
| 6,280,380 B1 | 8/2001 | Bardy | |
| 6,285,909 B1 | 9/2001 | Sweeney et al. | |
| 6,298,267 B1 | 10/2001 | Rosborough et al. | |
| 6,298,269 B1 | 10/2001 | Sweeney | |
| 6,298,272 B1 | 10/2001 | Peterfeso et al. | |
| 6,309,370 B1 | 10/2001 | Haim et al. | |
| 6,312,378 B1 | 11/2001 | Bardy | |
| 6,321,122 B1 | 11/2001 | Scheiner et al. | |
| 6,331,160 B1 | 12/2001 | Bardy | |
| 6,336,903 B1 | 1/2002 | Bardy | |
| 6,358,202 B1 | 3/2002 | Arent | |
| 6,358,203 B2 | 3/2002 | Bardy | |
| 6,361,522 B1 | 3/2002 | Scheiner et al. | |
| 6,361,780 B1 | 3/2002 | Ley et al. | |
| 6,363,281 B1 | 3/2002 | Zhu et al. | |
| 6,368,284 B1 | 4/2002 | Bardy | |
| 6,370,424 B1 | 4/2002 | Prutchi | |
| 6,388,043 B1 | 5/2002 | Langer et al. | |
| 6,398,728 B1 | 6/2002 | Bardy | |
| 6,400,982 B2 | 6/2002 | Sweeney et al. | |
| 6,411,840 B1 | 6/2002 | Bardy | |
| 6,411,844 B1 | 6/2002 | Kroll et al. | |
| 6,415,183 B1 | 7/2002 | Scheiner et al. | |
| 6,424,847 B1 | 7/2002 | Mastrototaro et al. | |
| 6,438,419 B1 | 8/2002 | Callaway et al. | |
| 6,440,066 B1 | 8/2002 | Bardy | |
| 6,442,413 B1 | 8/2002 | Silver | |
| 6,443,949 B2 | 9/2002 | Altman | |
| 6,453,195 B1 * | 9/2002 | Thompson | 607/3 |
| 6,459,917 B1 | 10/2002 | Gowda et al. | |
| 6,459,929 B1 | 10/2002 | Hopper et al. | |
| 6,468,263 B1 | 10/2002 | Fischell et al. | |
| 6,473,640 B1 | 10/2002 | Erlebacher | |
| 6,478,737 B2 | 11/2002 | Bardy | |
| 6,488,679 B1 | 12/2002 | Swanson et al. | |
| 6,501,983 B1 | 12/2002 | Natarajan et al. | |
| 6,511,477 B2 | 1/2003 | Altman et al. | |
| 6,518,245 B1 | 2/2003 | Anderson et al. | |
| 6,539,256 B1 | 3/2003 | KenKnight et al. | |
| 6,556,865 B2 | 4/2003 | Walcott et al. | |
| 6,571,125 B2 | 5/2003 | Thompson | |
| 6,604,000 B2 | 8/2003 | Lu | |
| 6,628,985 B2 | 9/2003 | Sweeney et al. | |
| 6,689,117 B2 | 2/2004 | Sweeney et al. | |
| 6,693,133 B1 | 2/2004 | Lopaschuk et al. | |
| 6,760,621 B2 | 7/2004 | Walcott et al. | |
| 6,766,195 B1 | 7/2004 | Bornzin et al. | |
| 6,802,811 B1 | 10/2004 | Slepian | |
| 6,824,561 B2 | 11/2004 | Soykan et al. | |
| 6,937,899 B2 | 8/2005 | Sheldon et al. | |
| 6,969,382 B2 | 11/2005 | Richter | |
| 6,976,982 B2 | 12/2005 | Santini, Jr. et al. | |
| 7,039,462 B2 | 5/2006 | Pastore et al. | |
| 7,072,711 B2 | 7/2006 | Girouard et al. | |
| 7,089,055 B2 | 8/2006 | Cates et al. | |
| 7,181,268 B2 | 2/2007 | Sheldon et al. | |
| 7,190,996 B2 | 3/2007 | Jarverud | |
| 7,201,733 B2 | 4/2007 | Scheiner et al. | |
| 7,302,294 B2 | 11/2007 | Kamath et al. | |
| 7,320,675 B2 | 1/2008 | Pastore et al. | |
| 7,340,303 B2 | 3/2008 | Zhu | |
| 7,369,890 B2 | 5/2008 | Lovett | |
| 7,392,090 B2 | 6/2008 | Sweeney et al. | |
| 7,425,210 B2 | 9/2008 | Sweeney et al. | |
| 7,539,533 B2 | 5/2009 | Tran | |
| 7,567,841 B2 | 7/2009 | Chan | |
| 7,577,478 B1 | 8/2009 | Kroll et al. | |
| 7,621,906 B2 | 11/2009 | Pastore et al. | |
| 7,764,995 B2 | 7/2010 | Girouard et al. | |
| 2001/0000802 A1 | 5/2001 | Soykan et al. | |
| 2001/0032085 A1 * | 10/2001 | Goedeke et al. | 704/275 |
| 2001/0051787 A1 | 12/2001 | Haller et al. | |
| 2002/0013612 A1 | 1/2002 | Whitehurst | |
| 2002/0026228 A1 | 2/2002 | Schauerte | |
| 2002/0031827 A1 | 3/2002 | Kanno et al. | |
| 2002/0035346 A1 | 3/2002 | Reynolds et al. | |
| 2002/0045809 A1 | 4/2002 | Ben-Haim | |
| 2002/0087116 A1 | 7/2002 | Hartlaub | |
| 2002/0091415 A1 | 7/2002 | Lovett et al. | |
| 2002/0099302 A1 | 7/2002 | Bardy | |
| 2002/0099328 A1 | 7/2002 | Scheiner et al. | |
| 2002/0107553 A1 | 8/2002 | Hill et al. | |
| 2002/0111551 A1 | 8/2002 | Van Erlach et al. | |
| 2002/0120306 A1 | 8/2002 | Zhu et al. | |
| 2002/0124855 A1 | 9/2002 | Chachques | |
| 2002/0161410 A1 | 10/2002 | Kramer et al. | |
| 2002/0169485 A1 | 11/2002 | Pless et al. | |
| 2003/0004403 A1 | 1/2003 | Drinan et al. | |
| 2003/0036773 A1 | 2/2003 | Whitehurst et al. | |
| 2003/0045805 A1 | 3/2003 | Sheldon et al. | |
| 2003/0060854 A1 | 3/2003 | Zhu | |
| 2003/0069606 A1 | 4/2003 | Girouard et al. | |
| 2003/0138415 A1 | 7/2003 | Shepard | |
| 2003/0149420 A1 | 8/2003 | Richter | |
| 2003/0153952 A1 | 8/2003 | Auricchio et al. | |
| 2003/0158584 A1 | 8/2003 | Cates et al. | |
| 2003/0167081 A1 | 9/2003 | Zhu et al. | |
| 2003/0208240 A1 | 11/2003 | Pastore et al. | |
| 2003/0233132 A1 | 12/2003 | Pastore et al. | |
| 2004/0002739 A1 | 1/2004 | Cates et al. | |
| 2004/0049235 A1 | 3/2004 | Deno et al. | |
| 2004/0059238 A1 * | 3/2004 | Fischell et al. | 600/515 |
| 2004/0059391 A1 | 3/2004 | Sweeney et al. | |
| 2004/0093034 A1 | 5/2004 | Girouard et al. | |
| 2004/0138648 A1 | 7/2004 | Sweeney et al. | |
| 2005/0043675 A1 | 2/2005 | Pastore et al. | |
| 2005/0137626 A1 | 6/2005 | Pastore et al. | |
| 2005/0192637 A1 | 9/2005 | Girouard et al. | |
| 2005/0283197 A1 | 12/2005 | Daum et al. | |
| 2005/0288721 A1 | 12/2005 | Girouard et al. | |
| 2006/0009811 A1 | 1/2006 | Sheldon et al. | |
| 2006/0015146 A1 | 1/2006 | Girouard et al. | |
| 2006/0247686 A1 * | 11/2006 | Girouard et al. | 607/3 |
| 2007/0276453 A1 | 11/2007 | Hill et al. | |
| 2008/0287818 A1 | 11/2008 | Shelchuk et al. | |
| 2009/0171228 A1 | 7/2009 | Fischell et al. | |
| 2009/0259268 A1 | 10/2009 | Chan | |

FOREIGN PATENT DOCUMENTS

| | | |
|---|---|---|
| EP | 0347708 A1 | 12/1989 |
| EP | 0467695 A2 | 1/1992 |
| EP | 0545628 A2 | 6/1993 |
| EP | 0550343 A1 | 7/1993 |
| EP | 0550344 A1 | 7/1993 |
| EP | 0620420 A1 | 10/1994 |
| EP | 0674916 A2 | 10/1995 |
| EP | 1050265 A2 | 11/2000 |
| EP | 1070516 A2 | 1/2001 |
| WO | WO-93/20888 A1 | 10/1993 |
| WO | WO-96/32984 A1 | 10/1996 |
| WO | WO-97/06854 A1 | 2/1997 |
| WO | WO-97/25098 A1 | 7/1997 |
| WO | WO-97/33513 A1 | 9/1997 |
| WO | WO-98/34537 A1 | 8/1998 |
| WO | WO-00/04947 A2 | 2/2000 |
| WO | WO-00/07497 A1 | 2/2000 |
| WO | WO-01/08748 A1 | 2/2001 |
| WO | WO-01/30436 A1 | 5/2001 |

OTHER PUBLICATIONS

"U.S. Appl. No. 10/742,574, Advisory Action mailed Apr. 24, 2009", 3 pgs.

"U.S. Appl. No. 10/742,574, Advisory Action mailed Aug. 11, 2008", 3 pgs.

"U.S. Appl. No. 10/742,574, Final Office Action mailed Jan. 15, 2010", 12 pgs.

"U.S. Appl. No. 10/742,574, Final Office Action mailed Feb. 18, 2009", 11 pgs.

"U.S. Appl. No. 10/742,574, Final Office Action mailed May 9, 2008", 12 pgs.

"U.S. Appl. No. 10/742,574, Non Final Office Action mailed Oct. 2, 2008", 12 pgs.

"U.S. Appl. No. 10/742,574, Non-Final Office Action mailed May 28, 2009", 12 pgs.

"U.S. Appl. No. 10/742,574, filed Jan. 17, 2008 to Non-Final Office Action mailed Oct. 17, 2007", 17 pgs.

"U.S. Appl. No. 10/742,574, filed Apr. 20, 2009 to Final Office Action mailed Feb. 18, 2009", 11 pgs.

"U.S. Appl. No. 10/742,574, filed Jul. 9, 2008 to Final Office Action mailed May 9, 2008", 16 pgs.

"U.S. Appl. No. 10/742,574, filed Sep. 10, 2008 to Final Office Action mailed May 9, 2008", 16 pgs.

"U.S. Appl. No. 10/742,574, filed Sep. 28, 2009 to Non Final Office Action mailed May 28, 2009", 11 pgs.

"U.S. Appl. No. 10/742,574, filed Dec. 22, 2009 to Non Final Office Action mailed Oct. 2, 2008", 11 pgs.

"U.S. Appl. No. 10/645,823, filed Dec. 12, 2006 to Restriction Requirement mailed Nov. 14, 2006", 16 pgs.

"U.S. Appl. No. 10/645,823 Restriction Requirement mailed Nov. 14, 2006", 5 pgs.

"U.S. Appl. No. 10/645,823 Non Final Office Action mailed Mar. 8, 2007", 8 pgs.

"U.S. Appl. No. 10/645,823 Notice of Allowance mailed Aug. 27, 2007", 7 pgs.

"U.S. Appl. No. 10/645,823, filed Jun. 8, 2007 to Non Final Office Action mailed Mar. 8, 2007", 19 pgs.

"U.S. Appl. No. 10/742,574, Non-Final Office Action mailed Oct. 17, 2007", 10 pgs.

"U.S. Appl. No. 10/742,574, filed May 12, 2006 to Restriction Requirement mailed Apr. 12, 2006", 16 pgs.

"U.S. Appl. No. 10/742,574, filed Sep. 25, 2007 to Final Office Action mailed Aug. 7, 2007", 17 pgs.

"U.S. Appl. No. 10/742,574, Restriction Requirement mailed Apr. 12, 2006", 7 pgs.

"U.S. Appl. No. 10/742,574 Advisory Action Mailed Dec. 21, 2006", 3 Pages.

"U.S. Appl. No. 10/742,574 Supplemental Amendment & Response filed Jan. 24, 2007 to Final Office Action Mailed Oct. 27, 2006 and Advisory Action dated Dec. 21, 2006", 17 pgs.

"U.S. Appl. No. 10/742,574 Final Office Action mailed Aug. 7, 2007", 12 pgs.

"U.S. Appl. No. 10/742,574 Final Office Action mailed Oct. 27, 2006", 14 pgs.

"U.S. Appl. No. 10/742,574 Non Final Office Action mailed Feb. 12, 2007", 13 pgs.

"U.S. Appl. No. 10/742,574 Non Final Office Action mailed May 23, 2006", 11 pgs.

"U.S. Appl. No. 10/742,574 Response filed May 14, 2007 to Non Final Office Action mailed Feb. 12, 2007", 15 pgs.

"U.S. Appl. No. 10/742,574 Response filed Aug. 23, 2006 to Non Final Office Action mailed May 23, 2006", 17 pgs.

"U.S. Appl. No. 10/742,574 Response filed Dec. 7, 2006 to Final Office Action mailed Oct. 27, 2006", 16 pgs.

Arnaud, C., et al., "iNOS is a Mediator of the Heat Stress-Induced Preconditioning Against Myocardial Infarction in vivo in the Rat", *Cardiovascular Research*, 58, (2003),118-125.

Bralet, J., et al., "Vasopeptidase Inhibitors: an Emerging Class of Cardiovascular Drugs", *Trends Pharmacol Sci.*, 22(3), (Mar. 2001), 106-109.

Brunner, F., "Attenuation of Myocardial Ischemia/Reperfusion Injury in Mice With Myocyte-Specific Overexpression of Endothelial Nitric Oxide Synthase", *Cardiovascular Research*, 57, (2003), 55-62.

Burns, B. E., "Fabrication Technology for a Chronic In-Vivo Pressure Sensor", *1984 International Electron Devices Meeting Technical Digest*, (1984), 210-212.

Carr, W. N., "Integrated Pressure Sensor with Remote Power Source and Remote Readout", *The 8th International Conference on Solid-State Sensors and Actuators and Eurosensors IX, Digest of Technical Papers*, Stockholm, Sweden, (Jun. 25-29, 1995), 624-627.

Chau, H.-L., "An Ultraminiature Solid-State Pressure Sensor for a Cardiovascular Catheter", *IEEE Transactions on Electron Devices*, (Dec. 1988),2355-2362.

Colonna, P., et al., "Myocardial Infarction and Left Ventricular Remodeling: Results of the CEDIM Trial", *Am Heart J.*, 139(2 Pt 3), (Feb. 2000), S124-S130.

Ferdinandy, P., et al., "Nitric oxide, superoxide, and peroxynitrite in myocardial ischaemia-reperfusion injury and preconditioning", *British Journal of Pharmocology*, 138(4), (2003),532-543.

Flogel, U., "Myoglobin: A scanvenger of bioactive NO", *PNAS*, 98(2), (Jan. 16, 2001),735-740.

Gewaltig, M. T., "Vasoprotection by nitric oxide: mechanisms and therapeutic potential", *Cardiovascular Research*, 55, (Feb. 14, 2002), 250-260.

Hada, Y., et al., "Pulsus alternans determined by biventricular simultaneous systolic time intervals", *Circulation*, 65(3), (Mar. 1982),617-26.

Lee, Y. C., et al., "Pulsus alternans in patients with congestive cardiomyopathy", *Circulation*, 65(7), (Jun. 1982),1533-1534.

Lehman, J, et al., "Gene regulatory mechanisms governing energy metabolism during cardiac hypertrophic growth", *Heart Fail Rev.*, (Apr. 2000),175-85.

Levin, L , "Researchers present findings at European cardiology conference", *Advisory Board Daily Briefing*, 8. Clinical Outlook, (Sep. 2002), 8 pgs.

Li, Q., "Gene Therapy With Inducible Nitric Oxide Synthase Protects Against Myocardial Infarction via a Cyclooxygenase-2-Dependent Mechanism", *Circulation Research*, 92, (2003),741-748.

Lopaschuk, G., "Metabolic abnormalities in the diabetic heart", *Heart Fail Rev.*, 7(2), (Apr. 2002), 149-59.

Lovett, E. G., "Technique for Discriminating Between Coordinated and Uncoordinated Cardiac Rhythms", U.S. Appl. No. 10/435,487, filed May 9, 2003, assigned to Cardiac Pacemakers, Inc., (May 9, 2003),36 pgs.

Luepker, R. V., et al., "Transthoracic Electrical Impedance: Quantitative Evaluation of a Non-Invasive Measure of Thoracic Fluid Volume", *American Heart Journal*, 85(1), (Jan. 1973),83-93.

Mai, J., "Enhanced Rate Response Algorithm for Orthostatic Compensation Pacing", *Pacing Clin Electrophysiol.* (PACE) Abstracts, 23 (Pt 2), (Apr. 2000),722.

Min, M., "Electrical Impedance and Cardiac Monitoring-Technology, Potential and Applications", *International Journal of Bioelectromagnetism*, 5(1), (2003),53-56.

Ostadal, P., et al., "The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003),45-50.

Paolocci, N., et al., "Positive inotropic and lusitropic effects of HNO/NO-in failing hearts: Independence from beta-adrenergic signaling", *Proceedings of the National Academy of Sciences USA*, 100(9), (Apr. 29, 2003),5537-5542.

Rizos, I , "Three-year survival of patients with heart failure caused by dilated cardiomyopathy and L-carnitine administration", *Am Heart J.*, 139(2 Pt 3), (Feb. 2000), S120-S123.

Rosborough, J. P., et al., "Electrical Therapy for Pulseless Electrical Activity", *NASPE*, 23(4), Part II, Abstract,(Apr. 2000),591.

Sabbah, H , et al., "Partial fatty acid oxidation inhibitors: a potentially new class of drugs for heart failure", *Eur J Heart Fail.*, 4(1), (Jan. 2002), 3-6.

Salloum, F., "Sildenafil Induces Delayed Preconditioning Through Inducible Nitric Oxide Synthase-Dependent Pathway in Mouse Heart", *Circulation Research*, 92, (Apr. 4, 2003), 595-597.

Schaefer, S., et al., "Clinical and hemodynamic characteristics of patients with inducible pulsus alternans", *American Heart Journal*, vol. 115, No. 6, (Jun. 1988), 1251-1257.

Smith, D., et al., "Influence of the Aortic Component of the Second Heart Sound on Left Ventricular Maximal Negative dP/dt in the Dog", *Am. J. Cardiol.*, 55: 205, (1985), 205-209.

Spiegel, E., "A CMOS Sensor and Signal Conversion Chip for Monitoring Arterial Blood Pressure and Temperature", *IEEE International Solid-State Circuits Conference,*, (Feb. 20, 1992),126-127.

Stanley, W., et al., "Energy metabolism in the normal and failing heart: potential for therapeutic interventions", *Heart Fail Rev.*, (Apr. 2002),115-30.

Stanley, W., "Partial fatty acid oxidation inhibitors for stable angina", *Expert Opin Investig Drugs*, 11(5), (May 2002),615-29.

Suematsu, Y., et al., "L-Arginine given after ischaemic preconditioning can enhance cardioprotection in isolated rat hearts", *European Journal of Cardio-thoracic Surgery*, 19, (2001),873-879.

Woldbaek, Per R., et al., "Increased cardiac IL-18 mRNA, pro-IL-18 and plasma IL-18 after myocardial infarction in the mouse; a potential role in cardiac dysfunction", *Cardiovascular Research*, 59, (2003),122-131.

Wolff, A , et al., "Metabolic approaches to the treatment of ischemic heart disease: the clinicians' perspective", *Heart Fail Rev.*, (Apr. 2002),187-203.

Wolfrum, S., et al., "Acute Reduction of Myocardial Infarct Size By a Hydroxymethyl Glutaryl Coenzyme A Reductase Inhibitor is Mediated By Endothelial Nitric Oxide Synthase", *J. Cardiovas Pharmacol*, vol. 41, No. 3, (Mar. 2003),474-480.

Wunderlich, C., "Acute Inhibition of Myoglobin Impairs Contractility and Energy State of iNOS-Overexpressing Hearts", *Circulation Research*, 92, (2003),1352-1358.

Wynn, R., "Cardiovascular drugs and dental considerations", *Cardiovascular drugs and dental considerations. J Calif Dent Assoc.*, 28(7), (Jul. 2000), 9-26.

Ziaie, B., "A Single-Channel Implantable Microstimulator for Functional Neuromuscular Stimulation", *IEEE Transactions on Biomedical Engineering*, 44, (Oct. 1997),909-920.

"U.S. Appl. No. 10/742,574, Advisory Action mailed May 3, 2010", 3 pgs.

* cited by examiner

METHOD AND APPARATUS FOR MODULATING CELLULAR METABOLISM DURING POST-ISCHEMIA OR HEART FAILURE

CROSS REFERENCE TO RELATED APPLICATION

This application is a divisional of U.S. application Ser. No. 10/645,823, filed Aug. 21, 2003, now U.S. Pat. No. 7,320,675, the entirety of which is incorporated herein by reference.

FIELD OF THE INVENTION

This document generally relates to cardiac rhythm management systems and particularly, but not by way of limitation, to such systems modulating cardiac cellular metabolism with drug delivery.

BACKGROUND

A heart is the center of a person's circulatory system. It includes a complex electro-mechanical system performing two major pumping functions. The left portions of the heart, including the left atrium and the left ventricle, draw oxygenated blood from the lungs and pump it to the organs of the body to provide the organs with their metabolic needs for oxygen. The right portions of the heart, including the right atrium and the right ventricle, draw deoxygenated blood from the organs and pump it into the lungs where the blood gets oxygenated. These pumping functions are accomplished by cardiac contractions, i.e., contractions of the myocardium (heart muscles).

Cardiac cells produces the energy required for the cardiac contractions from free fatty acids and glucose via aerobic metabolism. The energy production from glucose is more oxygen efficient than the energy production from fatty acids. In a normal adult heart, about 60-90% of the energy is produced from fatty acid oxidation. If the heart becomes ischemic, blood flow to the heart is reduced, resulting in insufficient oxygen supplying the aerobic metabolism of cardiac cells. In decompensated heart failure, glucose oxidation becomes the primary source of energy produced by the aerobic metabolism. During ischemia and compensated heart failure, fatty acids are still the primary source of energy, even though it is less oxygen-efficient than glucose. In both situations, the heart fails to maintain the normal rate of metabolism because of the reduced availability of oxygen. This results in a reduction of myocardial contractility, and hence, reduction of the heart's pumping efficiency and thus diminished blood flow.

Therefore, as a treatment for ischemia and heart failure, as well as related conditions and symptoms, there is a need to increase the rate of metabolism in cardiac cells in response to the reduced availability of oxygen.

SUMMARY

A drug delivery system detects a cardiac condition indicative of a need for increasing a cardiac metabolic level and, in response, releases a drug into tissue or blood to shift a source of metabolically synthesized energy fueling cardiac contraction from fatty acid to glucose. Such a system is applied to treat, for example, a patient suffering ischemia and/or heart failure or a patient having suffered myocardial infarction.

In one embodiment, a system includes a transdermal drug delivery device, an implantable cardiac rhythm management (CRM) device, and an external device. The implantable CRM device communicates with the transdermal drug delivery device and includes an ischemia detector, a drug level detector, and a drug delivery controller. The ischemia detector produces an ischemia indicating signal upon detection of an ischemia. The drug level detector detects a drug concentration in blood and produces an indication of the blood drug concentration. The external device communicates with the implantable CRM device and includes an external user input to receive an external user command. The drug delivery controller of the implantable CRM device controls the transdermal drug delivery device based on at least one of the ischemia indicating signal, the indication of the blood drug concentration, and the external user command.

In one embodiment, a system includes an implantable metabolic sensor, an implantable processor, and an implantable drug delivery device. The implantable metabolic sensor senses a metabolic signal indicative of a cardiac metabolic level. The implantable processor includes a metabolic sensor processing circuit and a drug delivery controller. The metabolic sensor processing circuit determines the cardiac metabolic level from the metabolic signal. The drug delivery controller produces a drug delivery signal based on the cardiac metabolic level. The implantable drug delivery device communicates with the implantable processor and delivers a drug in response to the drug delivery signal. The implantable drug delivery device includes a drug reservoir storing a drug shifting a source of metabolically synthesized energy for cardiac contractions from fatty acid to glucose.

In one embodiment, an implantable CRM device executing an automated ischemia detection algorithm is used to detect an ischemia. The implantable CRM device also detects an external user command directing a drug delivery. The external user command is transmitted from an external device. A drug delivery signal is produced upon a detection of at least one of the ischemia and the external user command. The drug delivery signal is transmitted to a transdermal drug delivery device. In response, a drug is delivered from the transdermal drug delivery device.

In one embodiment, a metabolic signal is sensed using an implantable sensor. A cardiac metabolic level is determined based on the metabolic signal using an implantable processor. A drug delivery signal is produced based on the cardiac metabolic level. The drug delivery signal is transmitted from the implantable processor to an implantable drug delivery device. In response, the implantable drug delivery device delivers a drug to shift a source of metabolically synthesized energy for cardiac contractions from fatty acid to glucose.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments

DETAILED DESCRIPTION

Figure 1:
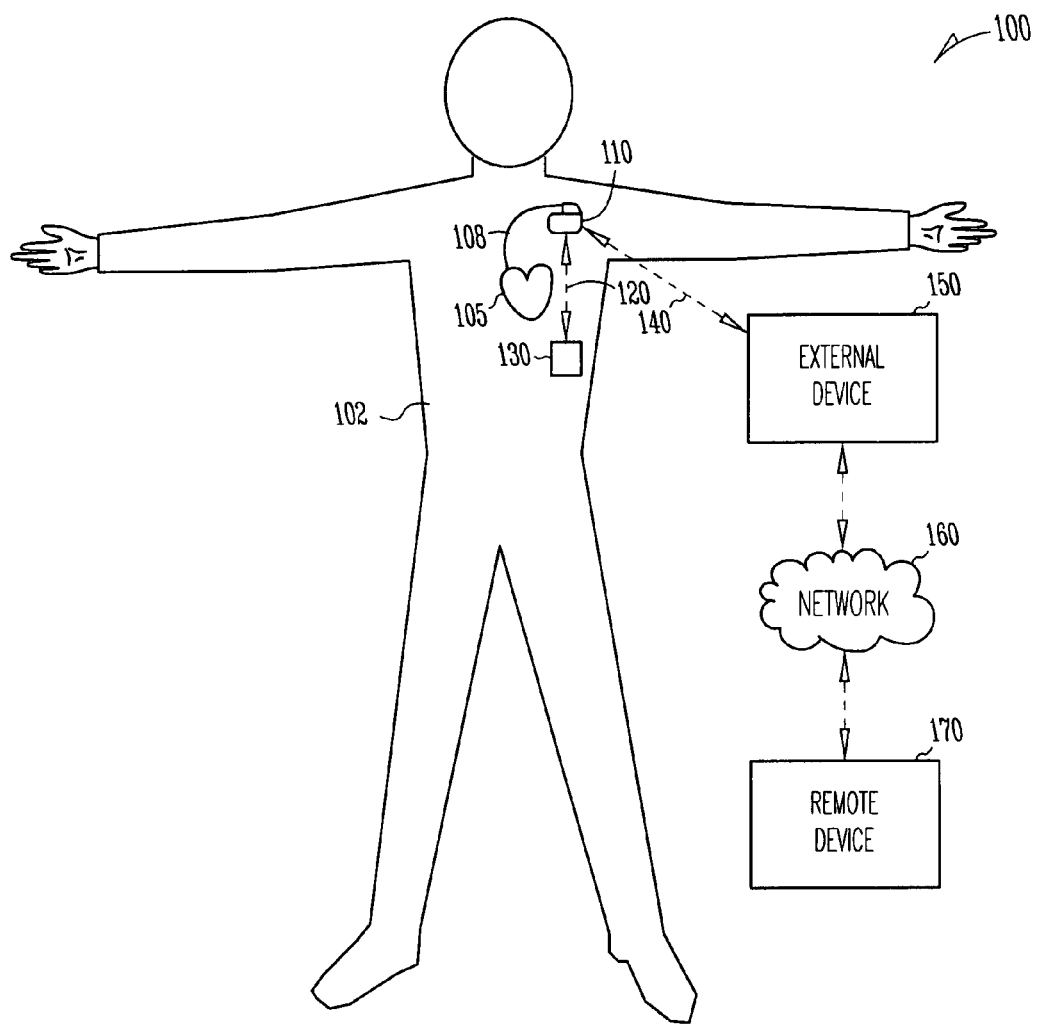
FIG. 1 is an illustration of an embodiment of a transdermal drug delivery system and portions of an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

Cardiac contraction is fueled by energy synthesized aerobically by cardiac cells from energy sources including glucose and free fatty acids. In normal adult hearts, the majority of the energy is produced from fatty acid oxidation. However, in certain cardiac disorders, decompensated heart failure for example, glucose becomes the primary energy source for aerobic metabolism. During ischemia and compensated heart failure, fatty acids are still the primary energy source even though fatty acids are less oxygen efficient than glucose. Pharmaceutical agents which shift metabolism from fatty acid oxidation to glucose oxidation are beneficial in patients with ischemia or heart failure, and, when administered chronically, are beneficial in heart failure or post-myocardial infarction patients. These pharmaceutical agents are generally most effective when administered in response to certain physiological signals and/or events, such as a change in cardiac metabolic level and/or an ischemic event. This is achieved by using a drug delivery system that detects the certain physiological signals and/or events and, in response, delivers one or more pharmaceutical agents that shift cardiac metabolism from fatty acid oxidation to glucose oxidation. The term "pharmaceutical agents," as used in this document, include agents that are chemical, biochemical, and/or biologic in nature.

Such a drug delivery system can be employed to deliver pharmaceutical agents to treat acute events, for instance, for relief of angina or heart failure decompensation, or to deliver pharmaceutical agents chronically to treat compensated heart failure or left ventricular dysfunction, or prophylactically to patients having previously suffered myocardial infarction. The pharmaceutical agents act upon cardiac cells to decrease the oxygen requirements to fuel cardiac metabolism by, for example, inhibiting or reducing fatty acid oxidation and/or increasing, enhancing, or stimulating pyruvate, glucose or lactate oxidation, preferably in cardiac cells. By decreasing the oxygen requirement for maintaining a normal or tolerable rate of cardiac metabolism by increasing its oxygen efficiency, the drug delivery system can be employed to minimize necrosis and apoptosis during chronic ischemia or an ischemic event.

In one embodiment, pharmaceutical agents within the scope of the present subject matter include, but are not limited to, those which shift metabolism from fatty acid oxidation to glucose oxidation, e.g., agents which decrease, inhibit (suppress) or reduce fatty acid oxidation (trimetazidine or ranolazine), and/or increase, enhance or stimulate pyruvate, glucose or lactate oxidation, preferably in cardiac cells. Thus, agents which inhibit lipolysis (nicotinic acid, aka niacin, and beta-adrenergic receptor antagonists), the rate of fatty acid release from fat cells, lower plasma fatty acid concentrations, uptake of fatty acids by the heart, entrance of fatty acids into the mitochodrion, for instance, by inhibiting CPT-1 (carnitine, L-propionylcarnitine, perhexyline, etomoxir, or oxfenicine), or inhibit the levels or activity of acyl-CoA dehydrogenase, e.g., long chain or medium chain acyl-CoA dehydrogenase, enoyl-CoA hydratase, 3-hydroxyacyl-CoA dehydrogenase, or beta-ketothiolase, or enhance the levels or activity of pyruvate dehydrogenase, e.g., dichlororacetate inhibits pyruvate dehydrogenase kinase, and increases cytosolic acetyl-CoA, which inhibits fatty acid oxidation, glucose (insulin) and/or lactate transporters or otherwise alter glucose transport (Akt-1) or stimulates insulin secretion (GLP-1). Acetyl CoA is converted to malonyl CoA, which inhibits carnitine palmitoyltransferase-1 (CPT-1), thereby reducing fatty acid uptake into mitochondria.

Those agents may be employed alone or in conjunction with other agents such as anti-hypertensive agents, anti-arrhythmic agents, pressors, vasopressors, vasodilators, anti-hyperlipidemic agents, anti-anginal agents, ionotropic agents, diuretics, volume expanders, thrombolytics, anti-platelet agents, beta-blockers, angiotensin converting enzyme (ACE) inhibitors, and angiotensin receptor blockers, or any combination thereof, including but not limited to diuretics such as thiazides, e.g., hydrochlorothizide, loop duretics, e.g., furosemide, and potassium-sparing agents, e.g., amiloride, sprionolactone and triamterene and hydrochlorothiazide, beta-blockers such as bisoprolol, carvedilol, labetolol and metoprolol, angiotensin-converting enzyme inhibitors such as benazepril, captopril, enalapril, fosinopril, lisinopril, perindopril, quinapril, ramipril, trandolapril, delapril, pentopril, moexipril, spirapril, temocapril, and imidapril, calcium channel blockers, alpha blockers, angiotensin II antagonists, e.g., losartan, statins, e.g., atorvastatin, pitavastatin, and pravastatin, or other lipid lowering agents, moxonidine, dihydropyridines, e.g., amlodipine, class III and IV antiarrhythmics, e.g., amiodarone, azimilide, sotalol, dofetilide, and ibutilide, aspirin, selective non-adrenergic imidazoline receptor inhibitors, nebivolol, vasopeptidase inhibitors, e.g., fasidotritat, omapatrilat, sampatrilat, substrates, inhibitors or inducers of cytochrome P450 enzymes, lidocaine, warfarin, oligonucleotides (sense or antisense), natriuretic peptides such as ANP, BNP, NT pro BNP, CNP, and DNP, colforsin daropate hydrochloride (forskilin derivative), antagonists of platelet integrin IIb/IIIa receptors, e.g., abciximab and trofiblant, reteplase, P2 receptor antagonists, e.g., ticlopidine and clopidogrel, mibefradil, hirudin, acetylcholinesterase inhibitors, cardiac glycosides, e.g., digoxin and digitoxin, bradykinin, neutral endopeptidease inhibitors, e.g., neprilysin, direct-acting vasodilators, e.g., hydralazine, nitroglycerin, sodium nitroprusside, catecholamines, dobutamine and dopamine, phosphodiesterase inhibitors, e.g., aminone and milrinone, TNFα, pentoxifyylline, growth hormone, cytokine inhibitors, aldosterone receptor antagonists, calcium sensitizers, nesiritide, 3,5-dicodothyropropionic acid, etomoxir, endothelin receptor antagonists, chlorthiadone, doxazosin, nesiritide, cilostazol, rilmenidine, ticlopidine, dihydropines such as nifedipine and nisoldipine, timolol, propanolol, verapamil, diltiazem, lisinopril, noopept (N-phenylacetyl-L-polyglycine ethylester), cariporide, geldanamycin, radicicol, ibudilast, selective delta (1) agonists such as 2-methyl-4a-alpha-(3-hydroxy-phenyl)-1,2,3,4,4a,5,12,12a-alpha-octahydroquinolinol [2,3,3-g]isoquinoline, monophosphoryl lipid A, RC552, adenosine, adenosine receptor agonists, adenosine triphosphate sensitive channel openers, dipyridamole, fibroblast growth factor, atenolol, ezetimibe, levosimendan, sirolimus, paclitaxel, actinomycin D, dexamethasone, tacrolimeus, everolimus, estradiol, quinapril, tranilast, angiopeptin, trapidil, lacidipine, thiazolidinediones, fenofibrate, lacidipine, nebivolol, nicotinic acid, probucol, rosuvastatin, gemfibrozil, glitazones, indobufen, alpha-tocopherol, dypiridamole, resins, e.g., cholestyramine and colestipol, bezafibrate, or listat, niacin, heparin, e.g., low molecular weight heparins such as dalteparin sodium and nadroparin calcium, bivalirudin, nitroglycerin, nicorandil, denopamine, eptifibatide, xemilofiban, or bofiban, trimetazidine, nicorandil, dalteparin, and isosorbide 5-mononitrate. Additional pharmaceutical agents may be considered based on evidence of their direct or indirect roles in preventing or reducing injury or hemodynamic compromise related to myocardial infarction and/or heart failure. Examples of such pharmaceutical agents include, but are not limited to, L-arginine; nitric oxide (NO); NO derivatives such as nitroxl anion (HNONO—) and peroxynitrite (ONOO—); iNOS, eNOS, and inhibitors such as nitro-L-arginine methyl ester; NO donors such as diethylamine (DEA) NO and nitroglycerin (NTG); and interleukins and interleukin inhibitors.

This document discusses, among other things, drug delivery systems each deliver a drug including one or more pharmaceutical agents shifting a source of metabolically synthesized energy for cardiac contractions from fatty acid to glucose. Specific examples of the one or more pharmaceutical agents include, but are not limited to, all pharmaceutical agents discussed in this document.

FIG. 1 is an illustration of an embodiment of a transdermal drug delivery system 100 and portions of an environment in which it is used. System 100 includes, among other things, an implantable cardiac rhythm management (CRM) device 110, a transdermal drug delivery device 130, an external device 150, and a remote device 170. As shown in FIG. 1, implantable CRM device is implanted in a body 102. Transdermal drug delivery device 130 is attached to the skin surface of body 102 at a site near heart 105. A lead system 108 provides electrical connection between heart 105 and implantable CRM device 110. A communication link 120 allows signal transmission between implantable CRM device 110 and transdermal drug delivery device 130. A telemetry link 140 provides for bidirectional communication between implantable CRM device 110 and external device 150. A network 160 provides for bidirectional communication between external device 150 and remote device 170.

System 100 allows a drug delivery to be triggered by any one of implantable CRM device 110, external device 150, and remote device 170. In one embodiment, implantable CRM device 110 triggers a drug delivery upon detecting a predetermined signal or condition. External device 150 triggers a drug delivery upon receiving an external user command from the patient wearing implantable CRM device 110 and transdermal drug delivery device 130 or from another person such as a relative, a friend, or a physician/caregiver. The patient enters the external user command when he or she detects an abnormal condition, such as a chest pain indicative of angina. Another person caring for the patient may also enter the external user command upon a request by the patient or an observation of an abnormal condition. Remote device 170 triggers a drug delivery upon receiving a remote user command from a physician/caregiver, who has been notified of the patient's condition. In other embodiments, external device 150 and/or remote device 170 process signals and/or a condition detected by implantable CRM device 110 to determine whether to trigger a drug delivery.

In one embodiment, system 100 is used for an acute treatment for relief of angina or heart failure decompensation. In another embodiment, system 100 is used to treat "silent myocardial infarctions" that are not detectable by the patient. A drug delivery is triggered upon detection of ischemia by implantable CRM device 110 and/or upon receiving an external user command from a patient in response to angina.

Figure 2:
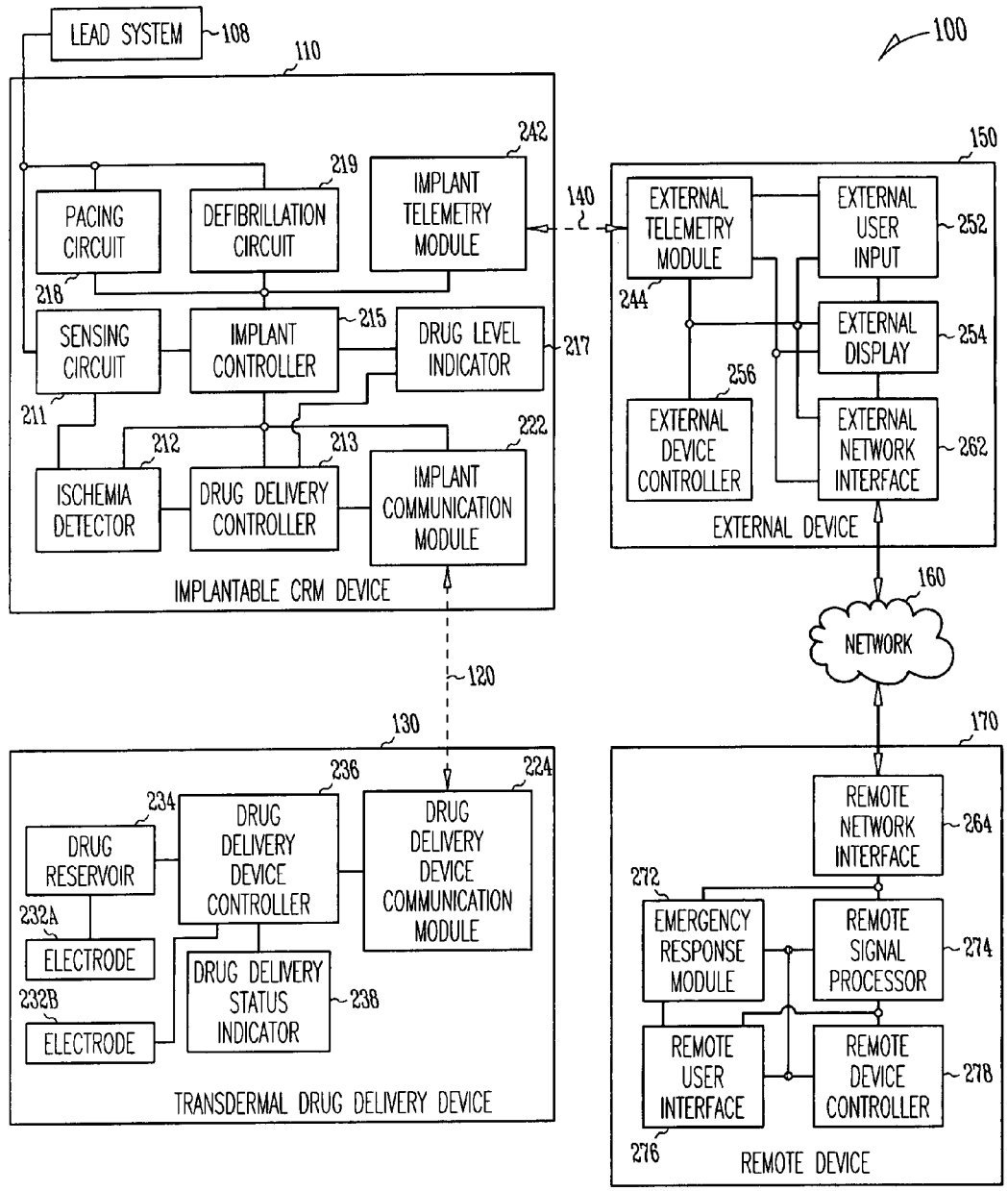
FIG. 2 is a block diagram showing one embodiment of the circuit of portions of the transdermal drug delivery system such as shown in FIG. 1.

FIG. 2 is a block diagram showing one embodiment of the circuit of portions of system 100. Implantable CRM device 110 as shown in FIG. 2 includes pacing and defibrillation capabilities. In addition to drug delivery, examples of therapies delivered by implantable CRM device 110 include, but are not limited to, bradyarrythmia pacing, anti-tachyarrhythmia pacing, atrial and/or ventricular cardioversion/defibrillation, cardiac resynchronization therapy, and cardiac remodeling control. However, the pacing and defibrillation capabilities are not necessary for system 100 to perform drug delivery, and hence, are not necessary elements of implantable CRM device 110. In other words, implantable CRM device 110 can be an implantable pacemaker and/or defibrillator with additional functions including control of drug delivery, or it can be a dedicated implantable drug delivery processor or controller.

In one embodiment, implantable CRM device 110 includes a sensing circuit 211, an ischemia detector 212, a drug delivery controller 213, a drug level indicator 217, a pacing circuit 218, a defibrillation circuit 219, an implant controller 215, an implant communication module 222, and an implant telemetry module 242. Sensing circuit 211 senses an intracardiac electrogram through a lead of lead system 108. Ischemia detector 212 detects an ischemia and produces an ischemia indicating signal when an ischemic condition is detected. In one embodiment, ischemia detector 212 has an input connected to sensing circuit 211 and an ischemia analyzer running an automatic ischemia detection algorithm to detect an ischemic condition from the electrogram. One specific example of an electrogram-based ischemia detector 212 is discussed in Zhu et al., U.S. patent application Ser. No. 09/962,852, entitled "EVOKED RESPONSE SENSING FOR ISCHEMIA DETECTION," filed on Sep. 25, 2001, assigned to Cardiac Pacemakers, Inc., which is incorporated herein by reference in its entirety. In another embodiment, ischemia detector 212 includes an electrical impedance based sensor using a low carrier frequency (e.g. 100 Hz) and an ischemia analyzer running an automatic ischemia detection algorithm to detect an ischemic condition from the electrical impedance signal. Tissue electrical impedance has been shown to increase significantly during ischemia, as discussed in Min, et al. *International Journal of Bioelectromagnetism*, 5(1): 53-56 (2003). Ischemia detector 212 senses low frequency electrical impedance signal between electrodes interposed in the heart, and detects the ischemia as abrupt changes in impedance (such as abrupt increases in value). In yet another embodiment, ischemia detector 212 includes a local heart motion based sensor utilizing an accelerometer located within a lead body positioned on or in the heart and an ischemia analyzer running an automatic ischemia detection algorithm to detect an ischemic condition from the acceleration signal. Ischemia detector 212 detects ischemia as an abrupt decrease in the amplitude of local cardiac accelerations. Upon receiving at least one of the ischemia indicating signal from ischemia detector 212, an external user command from external device 150, and a remote user command from remote device 170, drug delivery controller 213 generates a drug delivery signal. The drug delivery signal is transmitted through communication link 120 to transdermal drug delivery device 130 to trigger a drug delivery. After the drug delivery, drug level indicator 217 measures or estimates a blood drug concentration of the drug delivered to produce an indication of the blood drug concentration. In one embodiment, drug level indicator 217 includes a drug level detector that measures the blood drug concentration. In another embodiment, drug level indicator 217 includes a sensor measuring a physiological parameter indicative of the blood drug concentration. Examples of such a sensor include a respiration sensor and a heart rate detector. If drug level indicator 217 produces an indication of a blood drug concentration that is below a predetermined minimum level, drug delivery controller 213 produces a drug delivery signal to continue the drug delivery or start another drug delivery. Implant controller 215 provides for overall control and signal processing for implantable CRM device 110. Implant communication module 222 provides for a signal transmission interface allowing implantable CRM device 110 to communicate with transdermal drug delivery device 130, such as to transmit the drug delivery signal, via communication link 120. Implant telemetry module 242 provides for a telemetry interface allowing implantable CRM device 110 to communicate with external device 150 via telemetry link 140.

Lead system 108 includes one or more pacing leads, defibrillation leads, pacing-defibrillation leads, or any combination of such leads. It allows sensing of electrical signals from heart 105 and/or delivery of pacing pulses and/or defibrillation shocks to heart 105. In one embodiment, lead system 108 includes one or more transveous leads each having at least one sensing-pacing electrode disposed within heart 105. In one embodiment, lead system 108 includes one or more epicardial leads each having at least one sensing-pacing electrode disposed on heart 105. On one embodiment, lead system 108 includes one or more leads each having at least one sensor such as an accelerometer or a metabolic sensor. In one specific embodiment, lead system 108 includes one or more leads each having a metabolic sensor disposed in a blood pool when the lead is implanted.

Transdermal drug delivery device 130 includes electrodes 232A-B, drug reservoir 234, drug delivery device controller 236, drug delivery status indicator 238, and drug delivery communication module 224. One specific example of transdermal drug delivery device 130 is discussed in Scheiner et al., U.S. Pat. No. 6,361,522, entitled "DRUG DELIVERY SYSTEM FOR IMPLANTABLE CARDIAC DEVICE," assigned to Cardiac Pacemakers, Inc., which is incorporated herein by reference in its entirety. In one embodiment, transdermal drug delivery device 130 is a skin patch allowing electrically controlled transdermal drug delivery by, for example, iontophoresis, electroporation, electrorepulsion, or electro-osmosis. The skin patch is to be attached on a surface site of body 102 near heart 105. Electrodes 232A and 232B are skin-contact electrodes. Drug reservoir 234 contains the drug, which includes one or more pharmaceutical agents shifting a source of metabolically synthesized energy for cardiac contractions from fatty acid to glucose. Drug delivery status indicator 238 allows the patient and any other person such as a physician/caregiver to monitor, for example, whether the drug is being delivered and/or the amount of the drug remains in drug reservoir 234. Drug delivery device controller 236 controls the overall operation of transdermal drug delivery device 130. In one embodiment, drug delivery device controller 236 generates an electrical potential to cause the drug delivery upon receiving and/or decoding the drug delivery signal. Drug delivery communication module 224 provides for a signal transmission interface allowing transdermal drug delivery device 130 to communicate with implantable CRM device 110, such as to receive the drug delivery signal, via communication link 120.

Communication link 120 is supported by implant telemetry module 222 and drug delivery communication module 224. It allows communications between implantable CRM device 110 and transdermal drug delivery device 130. In one embodiment, communication link 120 is a telemetry link. In another embodiment, implantable CRM device 110 transmits electrical signals representative of the drug delivery signal into tissue of body 102, to be sensed through electrodes 232A-B and hence received by transdermal drug delivery device 130. In this embodiment, communication link 120 uses body 102 as the conductive medium for conducting electrical signals. One specific example of such a communication link is discussed in Sweeney et al., U.S. patent application Ser. No. 09/740,129, entitled "DRUG DELIVERY SYSTEM FOR IMPLANTABLE MEDICAL DEVICE," filed on Dec. 18, 2000, assigned to Cardiac Pacemakers, Inc., which is incorporated herein by reference in its entirety.

External device 150 includes an external user input 252, an external display 254, an external device controller 256, an external telemetry module 244, and an external network interface 262. External user input 252 receives the external user command from the patient or another person. In a further embodiment, it also receives other commands or instructions to control the operation of transdermal drug delivery device 130 and/or implantable CRM device 110. External device 150 transmits the external user command to implantable CRM device 110, resulting in a production of the drug delivery signal by drug delivery controller 213. In one embodiment, external device 150 also transmits the external user commands to remote device 170. In response, a remote user command directing a drug delivery may return from remote device 170. External device 150 relays the remote user command to implantable CRM device 110, resulting in a production of the drug delivery signal by drug delivery controller 213. External user input 252 includes a switch. In one embodiment, external user input 252 includes a push button. The patient pushes it, for example, when feeling a chest pain indicative of angina. In another embodiment, external user input 252 includes a voice controlled switch such that the patient may orally order a drug delivery. External telemetry module 244 provides for a telemetry interface allowing external device 150 to communicate with implantable CRM device 110 via telemetry link 140. External network interface 262 provides for a network interface allowing external device 150 to communicate with remote device 170 via network 160.

Telemetry link 140 is a wireless bidirectional data transmission link supported by implant telemetry module 242 and external telemetry module 244. In one embodiment, telemetry link 140 is an inductive couple formed when two coils—one connected to implant telemetry module 242 and the other connected to external telemetry module 244—are placed near each other. In this embodiment, the patient or another person places external device 150 on body 102 over implantable CRM device 110. In another embodiment, telemetry link 140 is a far-field radio-frequency telemetry link allowing implantable CRM device 110 and external device 252 to communicate over a telemetry range that is at least ten feet.

Remote device 170 includes an emergency response module 272, a remote signal processor 274, a remote user interface 276, a remote device controller 278, and a remote network interface 264. By executing one or more predetermined algorithms, remote signal processor 274 processes signals transmitted from external device 150 and signals transmitted from implantable CRM device 110. Emergency response module 272 contacts an emergency response unit, such as by calling 911 (in the United States), in response to an emergency situation as determined by one of implantable CRM device 110, external device 150, and remote device 170. In one embodiment, external device 150 transmits the external user command to remote device 170 as a request for contacting the emergency response unit through emergency response module 272. In another embodiment, remote signal processor 274 analyzes signals acquired by implantable CRM device 110 and transmitted to remote device 170, such as a portion of the electrogram sensed by sensing circuit 211, to determine the need for contacting the emergency response unit. In yet another embodiment, a physician/caregiver observes signals and/or the result of the analysis through remote user interface 276 to determine whether to contact the emergency response unit. Remote user interface 276 allows the physician/caregiver to enter a remote user command to be transmitted to transdermal drug delivery device 130. It also allows physician/caregiver to enter the remote user command to be transmitted to implantable CRM device 110 for a delivery or adjustment of pacing and/or defibrillation therapy. Remote device controller 278 controls the overall operation of remote device 170. In one embodiment, remote device controller 278 generates commands controlling one or more of transdermal drug delivery device 130, implantable CRM device 110, and external device 150 based on the received signals such as the portion of electrogram and the external user command. In one embodiment, remote device controller 278 executes an automatic algorithm to determine whether to issue a drug delivery command or to issue an electrical therapy (pacing and/or defibrillation, including cardiac resynchronization and/or remodeling control) command, such as when a physician/caregiver is not immediately available. Remote network interface 264 provides for an interface allowing communication between remote device 170 and external device 150 via network 160.

Network 160 provides long distance bi-directional communication between external device 150 and remote device 170. It allows management of multiple implantable devices, such as implantable CRM device 110 and transdermal drug delivery device 130, from a central facility at a remote location. In one embodiment, this allows prompt response by a physician/caregiver at the central facility as demanded by the condition of a patient. In one embodiment, network 160 is based on a wireless communications system. In another embodiment, network 160 is based on a wired communications system. In one embodiment, network 160 utilizes portions of a standard communications system such as the Internet, a telephone system, or a radio frequency telemetry system.

Figure 3:
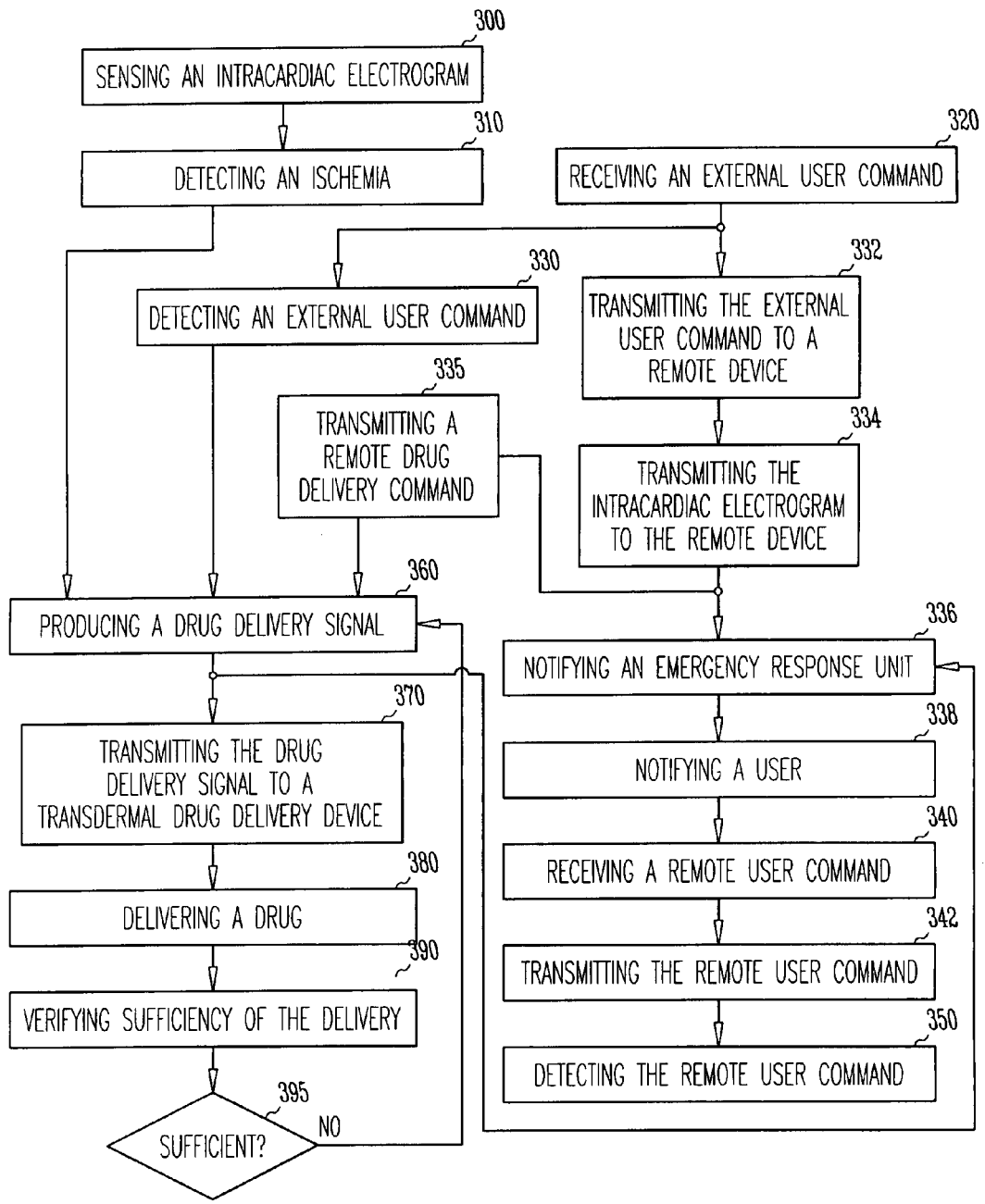
FIG. 3 is a flow chart illustrating an embodiment of a method for delivering a cardiac metabolism drug using the transdermal drug delivery system such as shown in FIG. 1.

FIG. 3 is a flow chart illustrating an embodiment of a method for delivering a drug using system 100. In one embodiment, the drug includes the one or more pharmaceutical agents shifting a source of metabolically synthesized energy for cardiac contractions from fatty acid to glucose, and the method is used as an acute treatment for relief of angina or heart failure decompensation. The method can also be used to treat "silent myocardial infractions" that are not detectable by the patient.

Sensing circuit 211 senses at least one electrogram from heart 105 at 300. Ischemia detector 212 detects an ischemia at 310, by executing an automated ischemia detection algorithm. In one embodiment, ischemia detector 212 detects an ischemia by executing an automated ischemia detection algorithm that analyzes the electrogram. When an ischemia is detected, ischemia detector 213 produces an ischemia indicating signal and sends it to drug delivery controller 213.

External user input 252 receives an external user command at 320. The patient enters the external user command by in response to chest pain indicative of angina. Alternatively, another person, such as a physician/caregiver, an attendant, or a relative, enter the external user command after determining that the patient should receive an immediate drug therapy. After external device 150 transmits the external user command to implantable CRM device 110, drug delivery controller 213 detects the external user command.

In one embodiment, in addition to transmitting the external user command to implantable CRM device 110, external device 150 transmits the external user command to remote device 170 though network 160 at 332. In one embodiment, remote device 170 also receives signals acquired by implantable CRM device 110, such as the electrogram, and transmits the signals to remote device 170 at 334. In one embodiment, after receiving the external user command and/or analyzing the signals acquired by implantable CRM device 110, remote device 170 notifies an emergence response unit, such as by calling 911 (as in the United States), at 336. In one embodiment, after receiving the external user command and/or analyzing the signals acquired by implantable CRM device 110, remote device 170 automatically produces a remote drug delivery command that is transmitted to implantable CRM device 110 through external device 150 at 335. In one embodiment, after receiving the external user command and/or analyzing the signals acquired by implantable CRM device 110, remote device 170 also notifies a user such as a physician/caregiver at 338. After the user makes a decision, remote device 170 receives a remote user command at 340. The remote user command directs a drug delivery and/or a delivery or adjustment of pacing (including such as cardiac resynchronization and remodeling control) or defibrillation therapy. Remote device 170 transmits the remote to external device 150 through network 160, and external device 150 relays the remote user command to implantable CRM device 110 at 342. Drug delivery controller 213 of implantable CRM device 110 detects the remote user command at 350.

Drug delivery controller 213 produces a drug delivery signal at 360, upon the detection of at least one of the ischemia, the external user command, the remote drug delivery command, and the remote user command. In one embodiment, the drug delivery signal is also transmitted to remote device 170 for notifying the emergency response unit and/or the user. Implantable CRM device 110 transmits the drug delivery signal to transdermal drug delivery device 130 at 370. In one embodiment, implantable CRM device 110 transmits the drug delivery signal the drug delivery signal via a telemetry link between implantable CRM device 110 and transdermal drug delivery device 130. In another embodiment, implantable CRM device 110 transmits an electrical signal representing the drug delivery signal to transdermal drug delivery device 130 via tissue conduction. In one specific embodiment, implantable CRM device 110 transmits a voltage signal representing the drug delivery signal into tissue of body 102 to be detected by transdermal drug delivery device 130.

In response to the drug delivery signal, transdermal drug delivery device 130 delivers a drug into tissue at 380. The drug includes one or more pharmaceutical agents shifting a source of metabolically synthesized energy for cardiac contractions from fatty acid to glucose. Then, drug level indicator 217 verifies that a sufficient amount of the drug has been delivered at 390, by detecting a signal indicative of a blood drug concentration. In one embodiment, this includes measuring a blood drug concentration directly. In another embodiment, this includes sensing a respiratory signal or measuring a heart rate. If drug level indicator 217 indicates that the blood drug concentration is below a predetermined level at 395, it produces an insufficiency alert signal and transmits it to drug delivery controller 213. Upon detection of the insufficiency alert signal, drug delivery controller 213 produces an additional drug delivery signal, and steps 360-395 are repeated until the drug level indicator 217 indicates that the blood drug concentration reaches the predetermined level at 395, or until a predetermined maximum dosage is reached.

Figure 4:
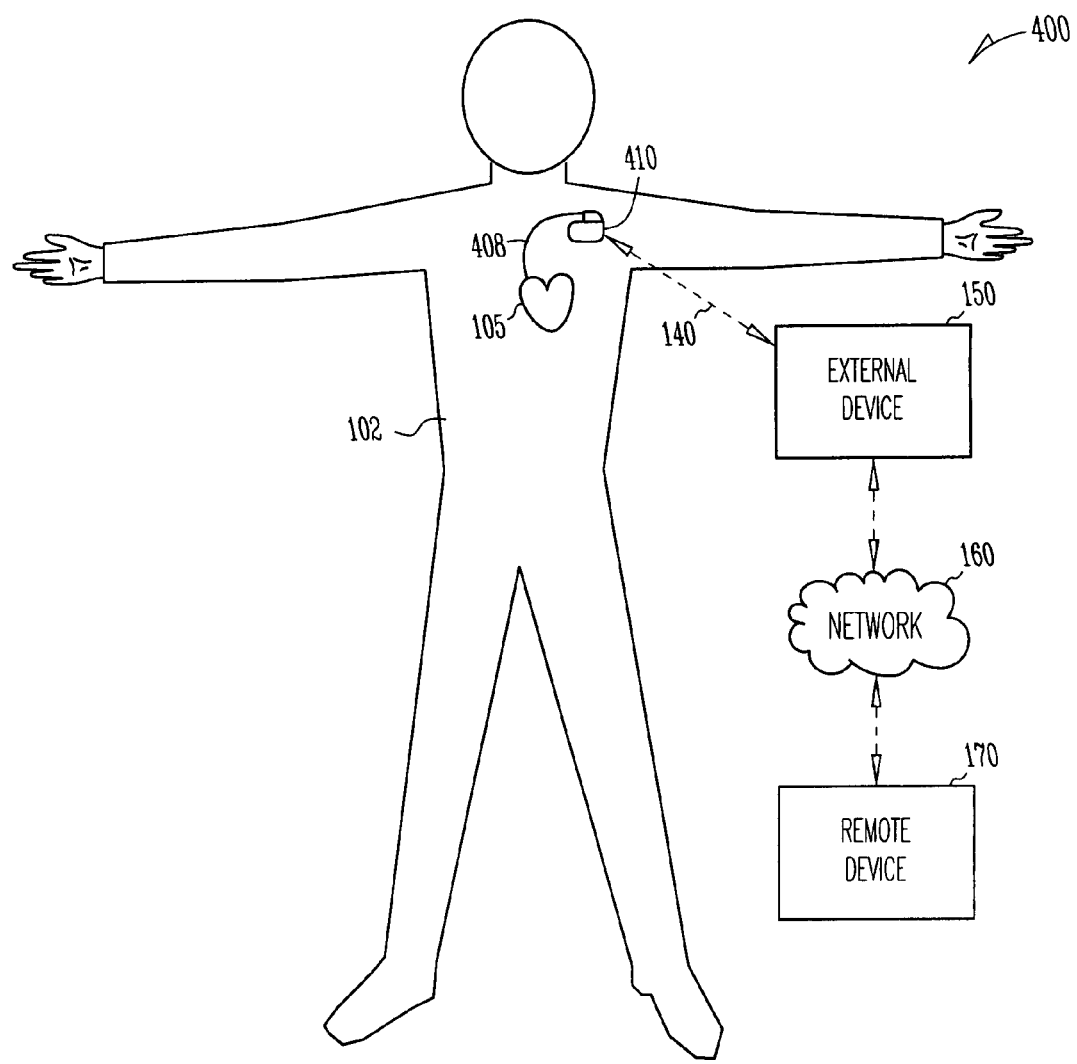
FIG. 4 is an illustration of an embodiment of an implantable drug delivery system and portions of an environment in which it is used.

FIG. 4 is an illustration of an embodiment of an implantable drug delivery system 400 and portions of an environment in which it is used. System 400 includes an implantable CRM device 410, which includes a drug delivery capability, and a drug eluting lead system 408. Identical numerals appearing in both FIGS. 1 and 4 indicate corresponding system components included in systems 100 and 400 that are structurally substantially identical.

System 400 allows a drug delivery to be triggered by any one of implantable CRM device 410, external device 150, and remote device 170. In one embodiment, implantable CRM device 410 triggers a drug delivery upon detecting a predetermined signal or condition. External device 150 triggers a drug delivery upon receiving an external user command from the patient wearing implantable CRM device 410 or from another person caring for the patient. Remote device 170 triggers a drug delivery upon receiving a remote user command from a physician/caregiver. In other embodiments, external device 150 and/or remote device 170 process signals and/or condition detected by implantable CRM device 410 to determine whether to trigger a drug delivery.

In one embodiment, system 400 is used for a chronic treatment for compensated heart failure or left ventricular dysfunction. In another embodiment, system 400 is used for a chronic treatment of patients having suffered myocardial infarction. A drug delivery is triggered upon detection that a change in the cardiac metabolic level exceeds a predetermined threshold. In one embodiment, a drug delivery is triggered upon detection that a change in the BNP level exceeds a predetermined threshold.

Figure 5:
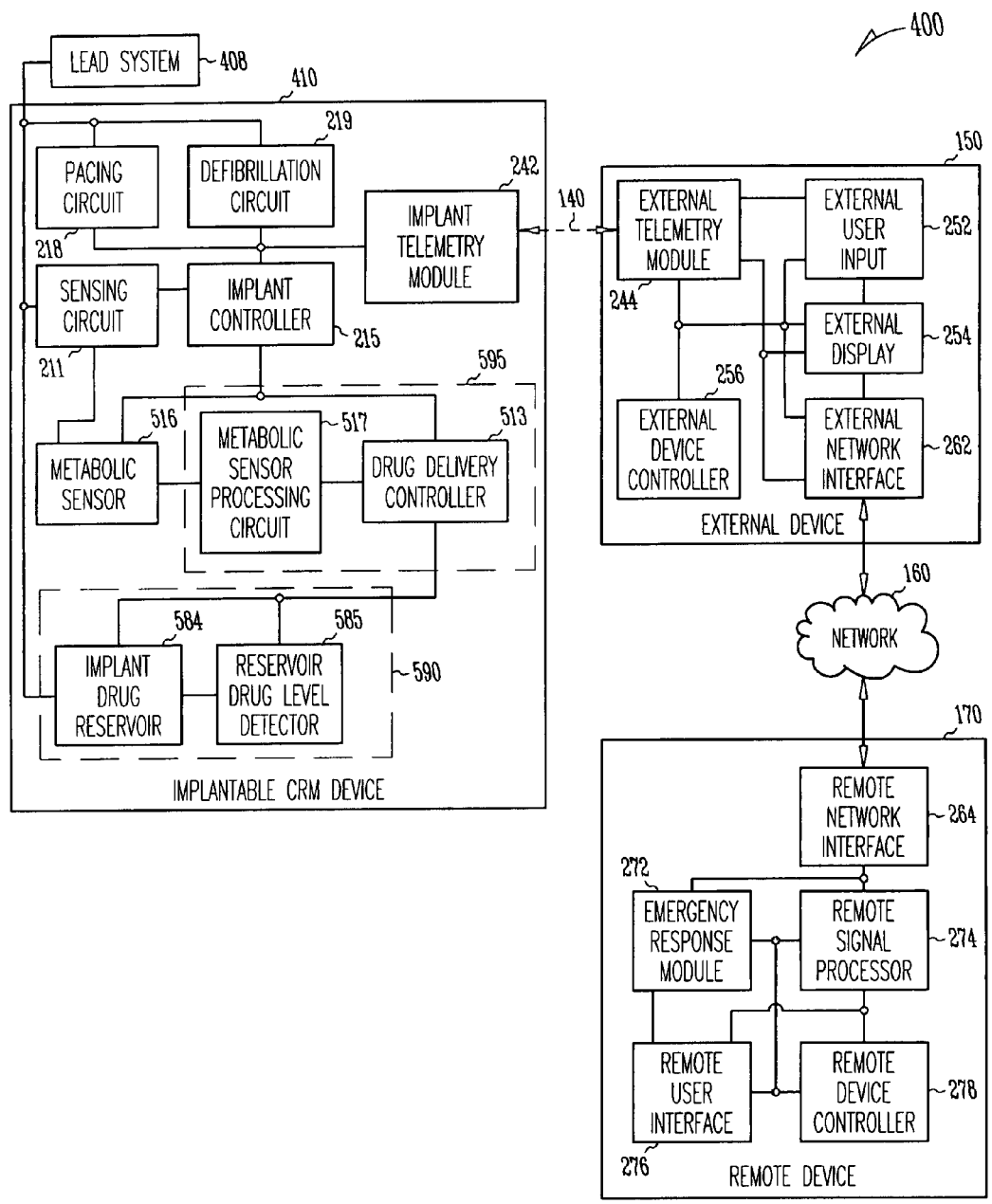
FIG. 5 is a block diagram showing one embodiment of the circuit of portions of the implantable drug delivery system such as shown in FIG. 4.

FIG. 5 is a block diagram showing one embodiment of the circuit of portions of system 400. While implantable CRM device 410 as shown in FIG. 5 includes pacing and defibrillation capabilities, such capabilities are not necessary for system 400 to perform drug delivery, and hence, are not necessary elements of implantable CRM device 410. In other words, implantable CRM device 410 can be a pacemaker and/or defibrillator with additional functions including control of drug delivery, or it can be an implantable drug delivery device.

In one embodiment, to perform the drug delivery function, implantable CRM device 410 includes an implantable metabolic sensor 516, an implantable processor 595 including a metabolic sensor processing circuit 517 and drug delivery controller 513, and an implantable drug delivery device 590 including an implant drug reservoir 584 and a reservoir drug level detector 585. In the embodiment shown in FIG. 5, implantable processor 595 and implantable drug delivery device 590 are functional modules housed within the same implantable housing. Metabolic sensor 516 senses a metabolic signal indicative of a cardiac metabolic level (rate of metabolism of cardiac cells). Examples of metabolic sensor 516 include a pH sensor, an oxygen pressure ($PO_2$) sensor, a carbon dioxide pressure ($PCO_2$) sensor, a glucose sensor, a creatine sensor, a C-creative protein sensor, a creatine kinase sensor, a creatine kinase-MB sensor, and any combination of such sensors. Metabolic sensor processing circuit 517 determines the cardiac metabolic level from the metabolic signal. Drug delivery controller 513 produces a drug delivery signal based on one or more of the cardiac metabolic level, the external user command, and the remote user command. Implant drug reservoir 584 contains the drug including the one or more pharmaceutical agents shifting a source of metabolically synthesized energy for cardiac contractions from fatty acid to glucose. Reservoir drug level detector 585 monitors the amount of the drug remaining in implant drug reservoir 584 and produces a drug-level-low alert signal when the amount of the drug is below a predetermined level. The drug-level-low alert signal is transmitted to remote device 170 to inform a physician/caregiver.

Lead system 408 includes at least one drug eluting lead connected to implant drug reservoir 584. In one embodiment, the drug eluting lead includes a fluid passageway having one opening at one end of the lead connected to implant drug reservoir 584 and another opening connected to a drug eluting electrode at or near the other end of the lead that is to be disposed in or about heart 105. The fluid passageway allows fluid communication between implant drug reservoir 584 and the location to which the drug is released. In one embodiment, where implant CRM device 410 has pacing and/or defibrillation capability, lead system 408 includes one or more pacing leads, defibrillation leads, pacing-defibrillation leads, or any combination of such leads. At least one of these leads includes the fluid passageway allowing drug delivery. Thus, lead system 408 allows sensing of electrical signals from heart 105 and/or delivery of pacing pulses and/or defibrillation shocks to heart 105, as well as delivering drug to heart 105. In one embodiment, lead system 408 includes an endocardial lead including at least one drug eluting electrode configured to be disposed within one of a coronary sinus and a portion of a great cardiac vein adjacent to the left ventricle of heart 105. In another embodiment, lead system 408 includes an epicardial lead including at least one drug eluting electrode configured to be attached to a portion of an epicardial wall of heart 105. In one embodiment, metabolic sensor 516 is built-in or attached to a lead of lead system 408, such that when the lead is implanted, metabolic sensor 516 is in a blood pool.

Telemetry link 140, external device 150, network 160, and remote device 170 in system 400 are substantially identical to the identically numbered elements of system 100, except that the signals acquired by implantable CRM device and transmitted to remote device 170 include the metabolic signal and/or the cardiac metabolic level. Remote device controller 278 of remote device 170 generates commands controlling one or more of implantable CRM device 410, including metabolic sensor 516, implantable processor 595, and implantable drug delivery device 590, and external device 150 based on the received signals and the remote user command.

Figure 6:
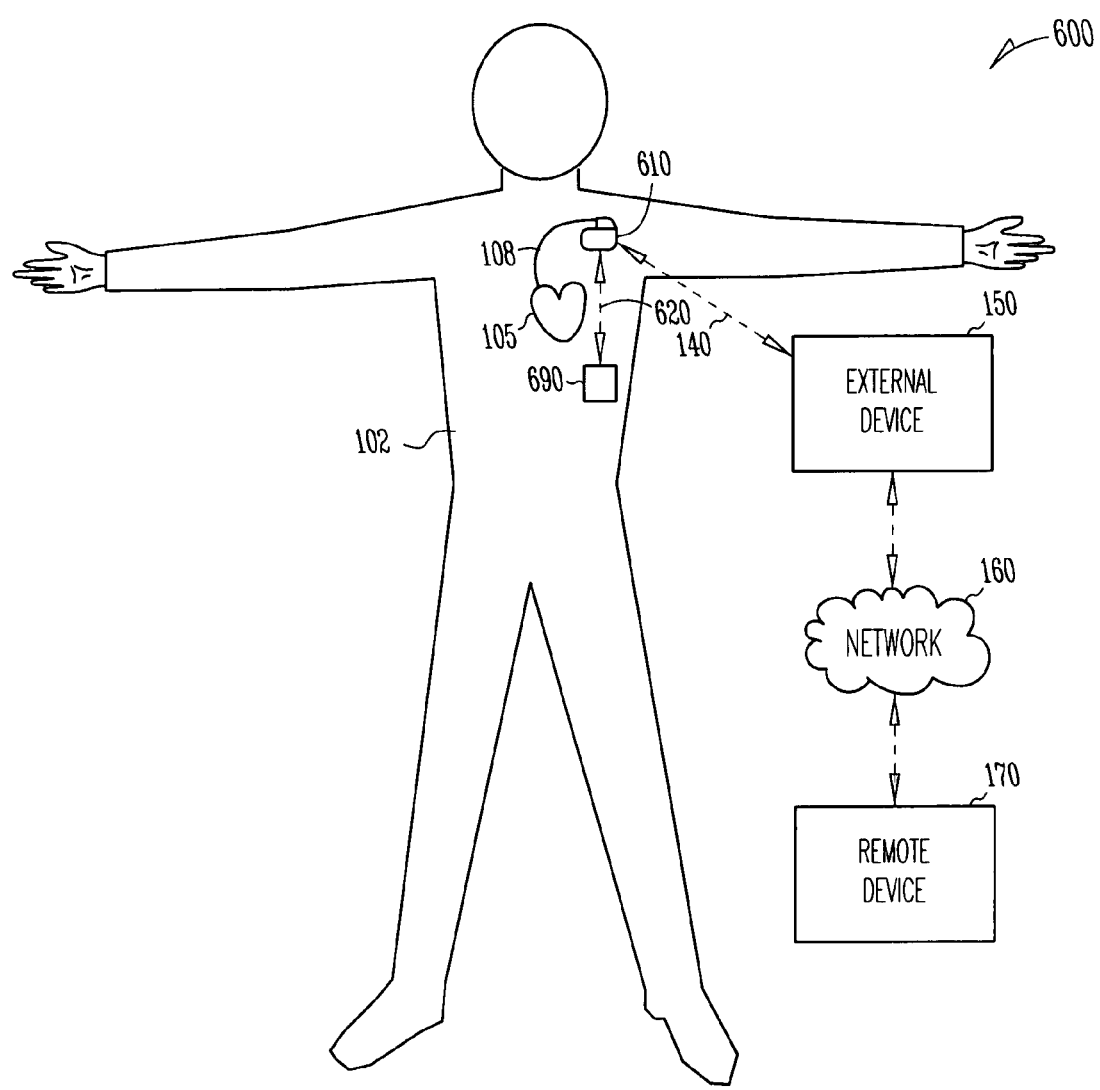
FIG. 6 is an illustration of another embodiment of an implantable drug delivery system and portions of an environment in which it is used.

FIG. 6 is an illustration of an embodiment of another implantable drug delivery system 600 and portions of an environment in which it is used. System 600 includes an implantable CRM device 610, an implantable drug delivery device 690, and a communication link 620 between the two devices. Identical numerals appearing in both FIGS. 4 and 6 indicate corresponding system components included in systems 400 and 600 that are structurally substantially identical. In one embodiment, system 600 differs from system 400 by having the implantable drug delivery device physically separate from the implantable CRM device.

System 600 allows a drug delivery to be triggered by any one of implantable CRM device 610, external device 150, and remote device 170. In one embodiment, implantable CRM device 610 triggers a drug delivery upon detecting a predetermined signal or condition. External device 150 triggers a drug delivery upon receiving an external user command from the patient wearing implantable CRM device 610 and implantable drug delivery device 690 or from another person caring for the patient. Remote device 170 triggers a drug delivery upon receiving a remote user command from a physician/caregiver. In other embodiments, external device 150 and/or remote device 170 process signals and/or condition detected by implantable CRM device 610 to determine whether to trigger a drug delivery.

In one embodiment, system 600 is used as a chronic treatment for compensated heart failure or left ventricular dysfunction. In another embodiment, system 600 is used as a chronic treatment of patients having suffered myocardial infarction. A drug delivery is triggered upon detection that a change in the cardiac metabolic level exceeds a predetermined threshold.

Figure 7:
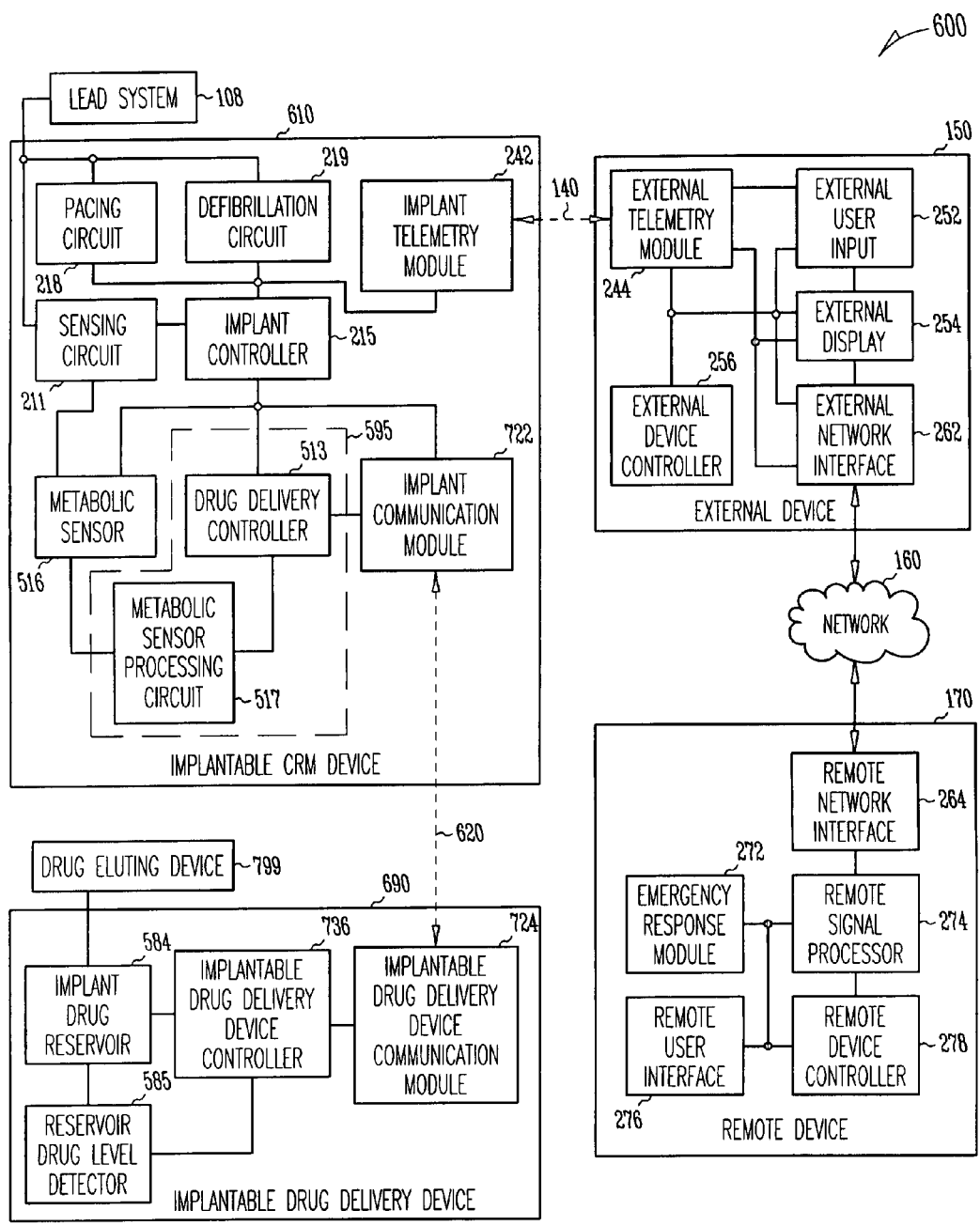
FIG. 7 is a block diagram showing one embodiment of the circuit of portions of the implantable drug delivery system such as shown in FIG. 6.

FIG. 7 is a block diagram showing one embodiment of the circuit of portions of system 600. While implantable CRM device 610 as shown in FIG. 5 includes pacing and defibrillation capabilities, such capabilities are not necessary for system 600 to perform drug delivery, and hence, are not necessary elements of implantable CRM device 610. In other words, implantable CRM device 410 can be a pacemaker and/or defibrillator with additional functions including control of drug delivery, or it can be an implantable processor dedicated to control of a separate implantable drug delivery device.

Implantable CRM device 610 generally retains implantable metabolic sensor 516 and implantable processor 595 of implantable CRM device 410, where implantable processor 595 includes a metabolic sensor processing circuit 517 and drug delivery controller 513. Implantable drug delivery device 590 of implantable CRM device 410 is replaced by a separate implantable device, that is, implantable drug delivery device 690.

Implantable drug delivery device 690 includes implant drug reservoir 584, reservoir drug level detector 585, implantable drug delivery device controller 736, and implantable drug delivery device communication module 724. Implantable drug delivery device controller 736 controls the overall operation of implantable drug delivery device 690. Implantable drug delivery device communication module 724 and an implant communication module 722 of implantable CRM device 610 support communication link 620. In one embodiment, communication link 620 is a telemetry link. In another embodiment, implantable CRM device 610 and transdermal drug delivery device 609 each transmit electrical signals into tissue of body 102, to be received by the other device through electrical conduction using tissue as the medium.

A drug eluting device 799 is connected to implant drug reservoir 584 to allow fluid communication between implant drug reservoir 584 and a body location to which the drug is released. In one embodiment, drug eluting device 799 includes at least one electrode connected to implant drug reservoir 584. In one specific embodiment, the electrode is disposed in blood to allow the drug to be released to the blood. In another specific embodiment, the electrode is disposed in tissue to allow the drug to be diffused into tissue. In one embodiment, drug eluting device 799 allows electrically controlled drug delivery by, for example, iontophoresis, electroporation, electrorepulsion, or electro-osmosis. In one embodiment, drug eluting device 799 includes a porous polymer that is sensitive to electric field applied on it. The drug is embedded in the polymer. Implantable drug delivery device controller 736 controls the drug delivery by controlling the electric field applied to the polymer. A change in the electric filed changes the size of the pores in the polymer and/or the binding affinity of the polymer, resulting in the release of the drug.

Implantable drug delivery device 690 and drug eluting device 799 can be incorporated to another implantable device (other than implantable CRM device 610). In one embodiment, implantable drug delivery device 690 and drug eluting device 799 are incorporated into or attached onto a coronary stent. In one specific example, the coronary stent is placed near an electrode from which electrical stimuli are delivered, such as a pacing electrode of lead system 108. The electrical stimuli (e.g., pacing pulses) cause the drug to release from drug eluting device 799, in response to the changing electric field created by the electrical stimuli.

Figure 8:
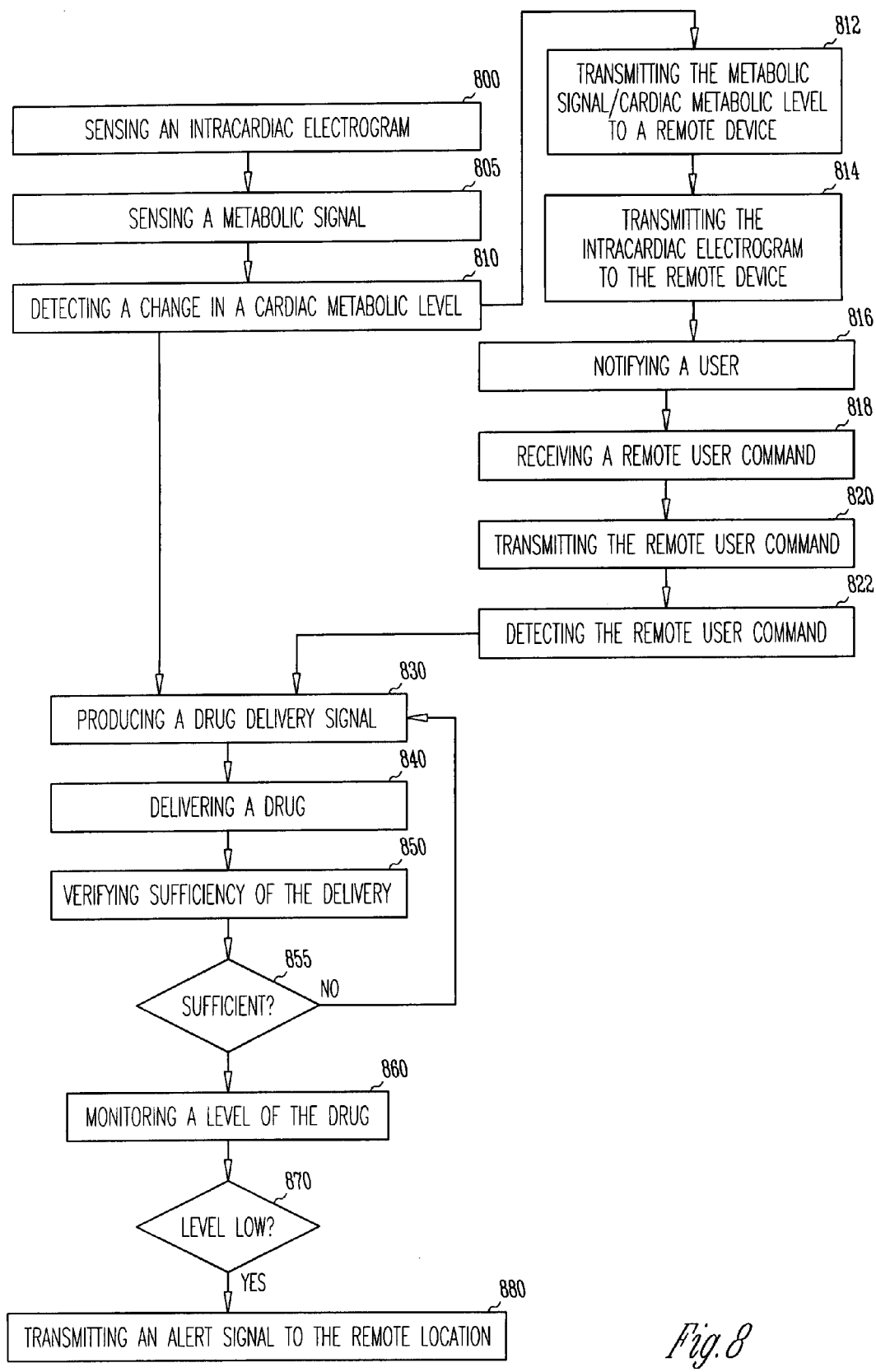
FIG. 8 is a flow chart illustrating an embodiment of a method for delivering a cardiac metabolism drug using one of the implantable drug delivery systems such as shown in FIGS. 4 and 6.

FIG. 8 is a flow chart illustrating an embodiment of a method for delivering a drug using either system 400 or system 600. In one embodiment, the drug includes the one or more pharmaceutical agents shifting a source of metabolically synthesized energy for cardiac contractions from fatty acid to glucose, and the method is used as a chronic treatment of compensated heart failure or left ventricular dysfunction. The method can be applied to treat patients having previously suffered myocardial infarction.

Sensing circuit 211 senses at least one electrogram from heart 105 at 800. Metabolic sensor 516 senses a metabolic signal at 805. In one embodiment, metabolic sensor 516 senses one or more of a blood pH level, a blood oxygen pressure ($PO_2$), a blood carbon dioxide pressure ($PCO_2$), a blood glucose level, a blood creatine level, a blood C-creative protein level, a blood creatine kinase level, and a blood creatine kinase-MB level. Metabolic sensor processing circuit 517 determines a cardiac metabolic level based on the metabolic signal, and detects a change in the cardiac metabolic level at 810. In one embodiment, metabolic sensor processing circuit 517 detects the change in the cardiac metabolism when the cardiac metabolic level exceeds a predetermined threshold. When the change in the cardiac metabolism is detected, metabolic sensor processing circuit 517 sends a signal indicative of the change to drug delivery controller 213.

In one embodiment, implantable CRM device 410 or 610 transmits the metabolic signal and/or the cardiac metabolic level to remote device 170 at 812. In one embodiment, this transmission is performed upon the detection of the change in the cardiac metabolism. In another embodiment, this transmission is performed in response to a request from remote device 170. In yet another embodiment, this transmission is performed on a predetermined schedule, such as on a periodic basis or when the patient is sleeping. In one embodiment, implantable CRM device 410 or 610 transmits additional acquired signals, such as a portion of the electrogram, to remote device 170 at 814. In one embodiment, after receiving the metabolic signal, the cardiac metabolic level, and/or the additional signals, remote device 170 notifies a user such as a physician/caregiver at 816. After the user makes a decision based on the signals received, remote device 170 receives a remote user command at 818. The remote user command directs a drug delivery and/or a delivery or adjustment of pacing or defibrillation therapy. Remote device 170 transmits the remote to external device 150 through network 160, and external device 150 relays the remote user command to implantable CRM device 410 or 610 at 820. Drug delivery controller 513 of implantable CRM device 410 or 610 detects the remote user command at 822.

Drug delivery controller 513 produces a drug delivery signal at 830, upon the detection of at least one of the changes in the cardiac metabolic level and the remote user command. In one embodiment with system 600, implantable CRM device 610 transmits the drug delivery signal to implantable drug delivery device 690 via telemetry or electrical conduction of the tissue intervening implantable CRM device 610 and implantable drug delivery device 690. In response to the drug delivery signal, implantable CRM device 410 or implantable drug delivery device 690 delivers the drug into tissue at 840. In one embodiment, this includes delivering the drug through a drug eluting lead, such as the drug eluting endocardial lead or the drug eluting epicardial lead. In another embodiment, this includes delivering the drug through a drug eluting stent. The drug includes the one or more pharmaceutical agents shifting a source of metabolically synthesized energy for cardiac contractions from fatty acid to glucose. Then, implantable CRM device 410 or 610 verifies that a sufficient amount of the drug has been delivered at 850, by monitoring the cardiac metabolic level after the drug delivery. If the cardiac metabolic level is below a predetermined threshold at 855, drug delivery controller 513 produces an additional drug delivery signal, and steps 830-855 are repeated until the cardiac metabolic level reaches the predetermined level at 855.

Reservoir drug level detector 585 monitors the level of the drug remaining in implant drug reservoir 584 at 860. If reservoir drug level detector 585 determines that the level is below a predetermined low threshold at 870, it produces a drug-level-low alert signal. The drug-level-low alert signal is transmitted to remote device 170 at 880. Subsequently, remote device 170 notifies a physician/caregiver.

It is to be understood that the above detailed description is intended to be illustrative, and not restrictive. For example, transdermal drug delivery device 130 can substitute for implantable drug delivery device 690. Although the present therapy is described in the example of cardiac therapy, it is understood that many other applications are possible. Systems 100, 400, and 600 may be generally applied in drug delivery controlled by a condition detected or a signal sensed from a person. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
   a transdermal drug delivery device adapted to deliver a drug;
   an implantable cardiac rhythm management (CRM) device communicatively coupled to the transdermal drug delivery device, the implantable CRM device including:
      an ischemia detector adapted to detect an ischemia and produce an ischemia indicating signal in response to a detection of the ischemia;
      a drug level detector including a respiratory sensor adapted to sense a respiratory signal as an indication of whether a blood drug concentration is below a predetermined minimum level after a delivery of the drug; and
      a drug delivery controller coupled to the ischemia detector and the drug level detector; and
   an external device communicatively coupled to the implantable CRM device, the external device including an external user input to receive an external user command,
   wherein the drug delivery controller is adapted to control the transdermal drug delivery device based on at least one of the ischemia indicating signal, the indication of the blood drug concentration, and the external user command.

2. The system of claim 1, wherein the implantable CRM device comprises a sensing circuit to sense at least one electrogram.

3. The system of claim 2, wherein the ischemia detector comprises an input coupled to the sensing circuit and an ischemia analyzer to produce the ischemia indicating signal based on an analysis of the at least one electrogram.

4. The system of claim 1, wherein the ischemia detector comprises:
   an impedance sensor to sense an electrical impedance signal; and
   an ischemia analyzer to produce the ischemia indicating signal based on an analysis of the electrical impedance signal.

5. The system of claim 1, wherein the ischemia detector comprises:
   an accelerometer to sense an acceleration signal; and
   an ischemia analyzer to produce the ischemia indicating signal based on an analysis of the acceleration signal.

6. The system of claim 1, further comprising:
   a remote device receiving signals including at least one of the external user command and the at least one electrogram; and
   a network coupled between the external device and the remote device to provide for bidirectional communication between the external device and the remote device.

7. The system of claim 6, wherein the remote device comprises an emergency response module adapted to contact an emergency response unit in response to the external user command.

8. The system of claim 6, wherein the remote device comprises a remote signal processor to process the received signals using at least one predetermined algorithm.

9. The system of claim 8, wherein the remote device further comprises a remote user interface providing for monitoring of the processed received signals and entry of remote user commands.

10. The system of claim 9, wherein the remote device further comprises a remote device controller adapted to generate commands controlling one or more of the transdermal drug delivery device, the implantable CRM device, and the external device based on the received signals and the remote user commands.

11. The system of claim 1, wherein the transdermal drug delivery device comprises a drug reservoir containing one or more pharmaceutical agents shifting a source of metabolically synthesized energy for cardiac contractions from fatty acid to glucose.

12. The system of claim 11, wherein the transdermal drug delivery device further comprises at least one skin contact electrode for transdermal drug delivery.

13. The system of claim 11, wherein the one or more pharmaceutical agents comprise one or more of agents decreasing, inhibiting, and/or reducing fatty acid oxidation and agents increasing, enhancing, and/or stimulating pyruvate, glucose, and/or lactate oxidation.

14. The system of claim 13, wherein the one or more pharmaceutical agents further comprise one or more of anti-hypertensive agents, anti-arrhythmic agents, pressors, vasopressors, vasodilators, anti-hyperlipidemic agents, anti-anginal agents, ionotropic agents, diuretics, volume expanders, thrombolytics, anti-platelet agents, beta-blockers, angiotensin converting enzyme (ACE) inhibitors, and angiotensin receptor blockers.

15. The system of claim 11, wherein the transdermal drug delivery device further comprises a drug delivery status indicator adapted to allow monitoring of whether the one or more pharmaceutical agents are being delivered.

16. The system of claim 11, wherein the transdermal drug delivery device further comprises a drug delivery status indicator adapted to allow monitoring of an amount of the one or more pharmaceutical agents remaining in the drug reservoir.

17. The system of claim 1, wherein the transdermal drug delivery device is configured to be a skin patch.

18. The system of claim 17, wherein the skin patch allows for electrically controlled transdermal drug delivery by iontophoresis, electroporation, electrorepulsion, or electro-osmosis.

19. The system of claim 1, wherein the external user input comprises a push button.

20. The system of claim 1, wherein the external user input comprises a voice controlled switch.

* * * * *

UNITED STATES PATENT AND TRADEMARK OFFICE
CERTIFICATE OF CORRECTION

| | |
|---|---|
| PATENT NO. | : 8,016,783 B2 |
| APPLICATION NO. | : 11/998969 |
| DATED | : September 13, 2011 |
| INVENTOR(S) | : Joseph M. Pastore et al. |

It is certified that error appears in the above-identified patent and that said Letters Patent is hereby corrected as shown below:

In column 4, line 33, delete "mitochodrion," and insert -- mitochondrion, --, therefor.

In column 4, line 34, delete "perhexyline," and insert -- perhexiline, --, therefor.

In column 4, line 39, delete "dichlororacetate" and insert -- dichloroacetate --, therefor.

In column 4, line 55, delete "hydrochlorothizide," and insert -- hydrochlorothiazide, -- therefor.

In column 4, line 56, delete "duretics," and insert -- diuretics, --, therefor.

In column 4, line 57, delete "sprionolactone" and insert -- spironolactone --, therefor.

In column 4, line 59, delete "labetolol" and insert -- labetalol --, therefor.

In column 5, line 7, delete "(forskilin" and insert -- (forskolin -- therefor.

In column 5, line 12, delete "endopeptidease" and insert -- endopeptidase --, therefor.

In column 5, line 15, delete "aminone" and insert -- amrinone --, therefor.

In column 5, line 19, delete "chlorthiadone," and insert -- chlorthalidone, --, therefor.

In column 5, lines 21-22, delete "propanolol," and insert -- propranolol, --, therefor.

In column 5, line 31, delete "tacrolimeus," and insert -- tacrolimus, --, therefor.

In column 5, line 35, delete "dypiridamole," and insert -- dipyridamole, --, therefor.

Signed and Sealed this
Twentieth Day of December, 2011

David J. Kappos
*Director of the United States Patent and Trademark Office*